United States Patent [19]

Aono et al.

[11] Patent Number: 5,770,772
[45] Date of Patent: Jun. 23, 1998

[54] INTERMEDIATES FOR THE PREPARATION OF AMINOCOUMARAN DERIVATIVES

[75] Inventors: Tetsuya Aono, Nagaokakyo; Shigenori Ohkawa, Takatsuki; Takayuki Doi, Izumi, all of Japan

[73] Assignee: Takeda Chemical Industries, Ltd., Osaka, Japan

[21] Appl. No.: 715,216

[22] Filed: Sep. 17, 1996

Related U.S. Application Data

[62] Division of Ser. No. 447,450, May 23, 1995, Pat. No. 5,594,154, which is a division of Ser. No. 305,717, Sep. 14, 1994, Pat. No. 5,478,844, which is a division of Ser. No. 784,988, Oct. 30, 1991, Pat. No. 5,376,681.

[30] Foreign Application Priority Data

Nov. 1, 1990 [JP] Japan ................................ 2-298650
Sep. 25, 1991 [JP] Japan ................................ 3-245667

[51] Int. Cl.⁶ .............................................. C07C 233/03
[52] U.S. Cl. ........................................ 564/218; 564/223
[58] Field of Search .................................. 564/223, 218

[56] References Cited

U.S. PATENT DOCUMENTS

| | | | |
|---|---|---|---|
| 3,547,931 | 12/1970 | Kaiser et al. ....................... | 260/294.8 |
| 3,686,188 | 8/1972 | Huebner .............................. | 260/294.8 |
| 4,772,459 | 9/1988 | Sun et al. ............................ | 424/10 |
| 4,772,730 | 9/1988 | Seelye et al. ....................... | 549/470 |
| 4,857,516 | 8/1989 | Terao et al. ........................ | 514/100 |
| 4,966,973 | 10/1990 | Goto et al. ......................... | 546/269 |
| 4,978,761 | 12/1990 | Goto et al. ......................... | 549/462 |
| 5,087,638 | 2/1992 | Belanger et al. ................... | 514/456 |

FOREIGN PATENT DOCUMENTS

| | | |
|---|---|---|
| 0 145 067 | 6/1985 | European Pat. Off. . |
| 0 147 044 | 7/1985 | European Pat. Off. . |
| 0 165 810 | 12/1985 | European Pat. Off. . |
| 0 234 872 | 9/1987 | European Pat. Off. . |
| 0 277 836 | 8/1988 | European Pat. Off. . |
| 0 281 261 | 9/1988 | European Pat. Off. . |
| 2 176 782 | 1/1987 | United Kingdom . |

OTHER PUBLICATIONS

Smith L. I. et al. J. Am. Chem. Soc. 62, 1863–1869, 1940.
Karakhanov E. A. et al. Izv. Vyssh. Ucheb. Zaved., Khim. Khim. Tekhnol. 16(4), 586–588, 1973.

*Primary Examiner*—Evelyn Huang
*Attorney, Agent, or Firm*—Foley & Lardner

[57] ABSTRACT

Disclosed are intermediates for the preparation of novel aminocoumaran derivatives of the general formula (I):

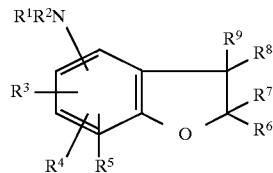

wherein $R^1$ and $R^2$ are a hydrogen atom, an acyl group, an alkoxycarbonyl group, an aliphatic group or aromatic group; $R^3$, $R^4$ and $R^5$ are an optionally acylated hydroxyl, optionally substituted amino group, alkoxy group or aliphatic group, or two of $R^3$, $R^4$ and $R^5$ may be linked together to form a carbocyclic group; $R^6$ and $R^7$ are an aliphatic group and at least one of them has a methylene group at the α-position; $R^8$ and $R^9$ are a hydrogen atom or an aliphatic group or aromatic group, or a salt thereof is useful for medicines for preventing and treating various diseases such as arterial sclerosis, hepatopathy, cerebrovascular diseases and the like.

2 Claims, No Drawings

INTERMEDIATES FOR THE PREPARATION OF AMINOCOUMARAN DERIVATIVES

This application is a division of application Ser. No. 08/447,450, filed May 23, 1995, U.S. Pat. No. 5,594,154, which is a divisional of Ser. No. 08/305,717 filed Sep. 14, 1994, U.S. Pat. No. 5,478,844, which is a divisional of Ser. No. 07/784,988 filed Oct. 30, 1991 U.S. Pat. No. 5,376,681.

FIELD OF THE INVENTION

The present invention relates to novel aminocoumaran derivatives or salts thereof and pharmaceutical compositions containing them as an active component. More specifically, the present invention relates to novel aminocoumaran derivatives or salts thereof and lipoperoxide formation inhibitory preparations containing them as an active component, which are useful as medicines for preventing and treating various diseases such as arterial sclerosis, hepatopathy, cerebrovascular diseases and the like.

BACKGROUND OF THE INVENTION

As it has become evident that the formation of a lipoperoxide in the body and a concomitant radical reaction have various harmful effects on the living body through membrane disorders, enzymatic disorders and the like, various attempts to use antioxidants and lipoperoxide formation inhibitors as medicines have been made. At present, the main lipoperoxide formation inhibitors used in the art are derivatives of natural antioxidants such as vitamin C, vitamin E and the like, and phenol derivatives (Kenji Fukuzawa, The Japanese Journal of Clinical Medicine, 46, 2269–2276, 1988). However, their fundamental structural skeletons are limited and they are not always satisfactory in practical use. Thus, it is desired to develop a lipoperoxide formation inhibitor having a novel structure that can be effectively and widely utilized in the medicinal field.

OBJECTS OF THE INVENTION

The main objects of the present invention is to provide novel compounds having a lipoperoxide formation inhibitory activity and lipoperoxide formation inhibitory preparations containing them as an active component.

SUMMARY OF THE INVENTION

Under these circumstances, the present inventors synthesized a number of novel compounds and tested their antioxidation activity and lipoperoxide formation inhibitory activity, respectively, in order to attain the above object.

As a result, the inventors have succeeded in creating aminocoumaran derivatives having a novel structure of the general formula (I):

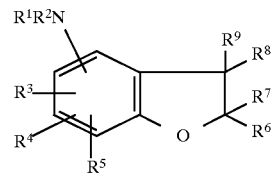

(I)

wherein $R^1$ and $R^2$ are the same or different and are a hydrogen atom, an acyl group, an alkoxycarbonyl group, an optionally substituted aliphatic or an optionally substituted aromatic group; $R^3$, $R^4$ and $R^5$ are the same or different and are an optionally acylated hydroxyl group, an optionally substituted amino group, an optionally substituted alkoxy group or an optionally substituted aliphatic group, or two of $R^3$, $R^4$ and $R^5$ may linked together to form an optionally substituted carbocyclic group; $R^6$ and $R^7$ are the same or different and are an optionally substituted aliphatic group, provided that at least one of $R^6$ and $R^7$ has methylene at the α-position; and $R^8$ and $R^9$ are the same or different and are a hydrogen atom or an optionally substituted aliphatic group or an optionally substituted aromatic group, or a salt thereof. Further, it has been found that the novel compounds have activities useful for medicines, for example, strong lipoperoxide formation inhibitory activity and the like. Thus, the present invention has been completed.

That is, the present invention provides the novel aminocoumaran derivatives of the general formula (I) or salts thereof and a pharmaceutical composition comprising them as an active component.

DETAILED DESCRIPTION OF THE INVENTION

In the general formula (I), the acyl group represented by $R^1$ and $R^2$ includes an acyl group derived from a carboxylic acid and an acyl group derived from a sulfonic acid and the like. As the acyl group derived from a carboxylic acid, there is a $C_{1-6}$ acyl group (e.g., formyl, acetyl, propionyl, butyryl, isobutyryl, valeryl, etc.). As the acyl group derived from a sulfonic acid, there is a $C_{1-3}$ alkylsulfonyl group such as methanesulfonyl, ethanesulfonyl, propanesulfonyl and the like and phenylsulfonyl group. As the alkoxycarbonyl group represented by $R^1$ and $R^2$, there are a lower alkoxycarbonyl group the alkoxy of which has 1 to 5 carbon atoms such as methoxycarbonyl group, ethoxycarbonyl group and the like. The aliphatic group represented by $R^1$ and $R^2$ may be a saturated or unsaturated group and examples thereof include an alkyl group, an alkenyl group and an alkynyl group. The alkyl group may be straight, branched or cyclic. Among the alkyl groups, a lower alkyl group having 1 to 6 carbon atoms is preferred and the examples thereof include methyl, ethyl, i-propyl, butyl, i-butyl, t-butyl, pentyl, hexyl, cyclopropyl, cyclobutyl, cyclopentyl and the like. As the alkenyl group represented by $R^1$ and $R^2$, in general, that having 2 to 6 carbon atoms is preferred and examples thereof include allyl, propenyl, i-propenyl, 2-butenyl, 2,4-butadienyl, 2-pentenyl and the like. As the alkynyl group represented by $R^1$ and $R^2$, in general, that having 2 to 6 carbon atoms is preferred and examples thereof include ethynyl, 2-propynyl and the like. The substituents which these aliphatic groups may have are not especially limited. As the substituents, any groups which can normally be used for medicines may be used and examples thereof include hydroxyl, $C_{1-3}$ alkoxy (e.g., methoxy, ethoxy, n-propoxy or iso-propoxy, etc.), aralkyloxy (phenyl-$C_{1-6}$ alkyloxy or naphthyl-$C_{1-6}$ alkyloxy, e.g., benzyloxy, phenethyloxy, etc.), aryloxy (e.g., phenyloxy, naphthyloxy, pyridyloxy, imidazolyloxy, etc.), mercapto, $C_{1-3}$ alkylthio (e.g., methylthio or ethylthio, etc.), $C_{1-3}$ alkylsulfonyl (e.g., methylsulfonyl or ethylsulfonyl, etc.), $C_{1-3}$ alkylsulfinyl (e.g., methylsulfinyl or ethylsulfinyl, etc.), aralkylthio (phenyl-$C_{1-6}$ alkylthio or naphthyl-$C_{1-6}$ alkylthio, e.g., benzylthio, phenethylthio, etc.), aralkylsulfonyl (phenyl-$C_{1-6}$ alkylsulfonyl or naphthyl-$C_{1-6}$ alkylsulfonyl, e.g., benzylsulfonyl, phenethylsulfonyl, etc.), aralkylsulfinyl (phenyl-$C_{1-6}$ alkylsulfinyl or naphthyl-$C_{1-6}$ alkylsulfinyl, e.g., benzylsulfinyl, phenethylsulfinyl, etc.), arylthio (e.g., phenylthio, naphthylthio, pyridylthio, imidazolylthio, etc.), arylsulfonyl (e.g., phenylsulfonyl, naphthylsulfonyl, pyridylsulfonyl or imidazolylsulfonyl, etc.), arylsulfinyl (e.g., phenylsulfinyl, naphthylsulfinyl, pyridylsulfinyl or imidazolylsulfinyl, etc.), amino, mono- or di-substituted amino which is substituted with 1 or 2 groups of $C_{1-3}$ alkyl, aralkyl (phenyl-$C_{1-6}$ alkyl or naphthyl-$C_{1-6}$ alkyl, etc.) and aryl (phenyl, naphthyl, pyridyl or imidazolyl, etc.) (e.g., methylamino, ethylamino, dimethylamino, benzylamino, phenylamino, pyridylamino, etc.), halogen (e.g., chloro or fluoro), esterified carboxyl [e.g., $C_{2-5}$ alkoxycarbonyl (e.g., methoxycarbonyl, ethoxycarbonyl, etc.)], $C_{2-3}$ acyl (e.g., acetyl, propionyl, etc.), $C_{2-3}$ acyloxy (e.g., acetoxy, propionyloxy, etc.), $C_{2-3}$ acylamino (e.g., acetamido, etc.), $C_{2-5}$ alkoxycarbonylamino (e.g., methoxycarbonylamino, ethoxycarbonylamino, etc.), a cyclic amino group (e.g., pyrrolidino, morpholino, piperazino, etc.), a carboxyl group, a carbamoyl group and the like. The number of these substituents is preferably 1 to 2.

As the aromatic group represented by $R_1$ and $R_2$, there is a phenyl group. Examples of the substituent on the phenyl group include an amino group, a mono- or di-alkylamino group substituted with a $C_{1-3}$ lower alkyl group, halogen, nitro, sulfo, cyano, hydroxyl, carboxyl, $C_{1-5}$ lower alkyl, $C_{1-3}$ lower alkoxy, $C_{2-5}$ acyl, $C_{1-3}$ lower alkylmercapto and the like. The number of the substituents is not limited but is preferably 1 to 3.

The group represented by $-NR^1R^2$ may substitute the benzene ring of the coumaran at any position of the ring, preferably at the 5-position of the coumaran.

It is preferable that one of $R^1$ and $R^2$ is a hydrogen atom and the other is a hydrogen atom, a phenyl group or a straight, branched or cyclic $C_{1-6}$ alkyl group.

When the hydroxyl group represented by $R^3$, $R^4$ and $R^5$ is acylated, the acyl group includes a $C_{2-5}$ straight or branched carboxylic acid acyl group (e.g., acetyl, propionyl, butyryl, isobutyryl, etc.). When the amino group represented by $R^3$, $R^4$ and $R^5$ has substituents, examples of the substituents include those of the optionally substituted aliphatic or aromatic groups represented by $R^1$ and $R^2$. As the alkoxy group represented by $R^3$, $R^4$ and $R^5$, there is a $C_{1-6}$ straight or branched alkyl group or an alkoxy group composed of a cyclic alkyl group. As the substituent of the alkoxy group, there are, for example, an amino group, a mono- or di-alkylamino group substituted with a $C_{1-3}$ lower alkyl group, halogen, hydroxyl, lower alkoxy, lower alkylmercapto and the like. Examples of the aliphatic group represented by $R^3$, $R^4$ and $R^5$ and the substituents thereof include the groups described with respect to the aliphatic group represented by $R^1$ and $R^2$. Two of $R^3$, $R^4$ and $R^5$ may linked together to form an optionally substituted carbocyclic group and, in this case, a 5- or 6-membered carbocyclic group is preferred. Examples of the substituents thereof include a $C_{1-3}$ alkyl group, a $C_{1-3}$ alkoxy group, hydroxyl group and the like.

$R^3$, $R^4$ and $R^5$ are preferably straight, branched or cyclic $C_{1-6}$ alkyl groups.

Examples of the aliphatic group represented by $R^6$ and $R^7$ include the groups described with respect to $R^1$ and $R^2$. The substituent of the aliphatic group represented by $R^6$ and $R^7$ includes an optionally substituted aromatic group in addition to the substituents described with respect to he aliphatic group represented by $R^1$ and $R^2$. The optionally substituted aromatic groups and the substituent thereof include those described with respect to $R^1$ and $R^2$. Further, at least one of $R^6$ and $R^7$ has methylene group at the α-position. In other words, $R^6$ and $R^7$ are optionally substituted aliphatic groups and at least one of them are a group of the formula $-CH_2R'$ wherein R' is hydrogen or R' together with $-CH_2$ form an optionally substituted aliphatic group. Examples of such an aliphatic group and its substituent include those exemplified with respect to the groups $R^6$ and $R^7$.

It is preferable that one of $R^6$ and $R^7$ is a straight, branched or cyclic $C_{1-6}$ alkyl group, and the other is a straight, branched or cyclic $C_{1-6}$ alkyl group or aralkyl group (preferably phenyl-$C_{1-6}$ alkyl or naphthyl-$C_{1-6}$ alkyl such as benzyl, phenethyl, phenylpropyl or the like) which may be substituted with a group having 1 to 5 hetero atoms (N, S, O). Examples of the group having 1 to 5 hetero atoms are $C_{1-3}$ alkoxy, aralkyloxy, aryloxy, $C_{1-3}$ alkylthio, $C_{1-3}$ alkylsulfonyl, $C_{1-3}$ alkylsulfinyl, aralkylthio, aralkylsulfonyl, aralkylsulfinyl, arylthio, arylsulfonyl, arylsulfinyl, mono- or di-substituted amino which is substituted with 1 or 2 groups of $C_{1-3}$ alkyl, aralkyl and aryl, and cyclic amino groups.

The aliphatic group represented by $R^8$ and $R^9$ includes that described with respect to $R^6$ and $R^7$. The aromatic group represented by $R^8$ and $R^9$ includes that described with respect to $R^1$ and $R^2$.

It is preferable that one of $R^8$ and $R^9$ is a hydrogen atom and the other is a phenyl group optionally substituted with a hydrogen atom, halogen or a straight, branched or cyclic $C_{1-6}$ alkyl group, or a straight, branched or cyclic $C_{1-6}$ alkyl group.

The compound represented by the general formula (I) may have its stereoisomer depending upon a particular kind of the substituent. The present invention includes not only one isomer but also the mixture thereof.

Salts of the compounds represented by the general formula (I) are preferably pharmaceutically acceptable salts, and examples of the pharmaceutically acceptable salt include those formed with inorganic acids such as hydrohalogenic acid (e.g., hydrochloric acid, hydrobromic acid, etc.), phosphoric acid, sulfuric acid and the like, and organic acids such as organic carboxylic acids (e.g., oxalic acid, phthalic acid, fumaric acid, maleic acid, etc.), sulfonic acids (e.g., methanesulfonic acid, benzenesulfonic acid) and the like. Further, when the compounds (I) contain acidic groups such as carboxyl group and the like as the substituents, the salts include inorganic base salts formed with alkaline metals (e.g., sodium, potassium, etc.) or alkaline earth metals (e.g., magnesium) and the like and salts formed with organic bases (e.g., amines such as dicyclohexylamine, triethylamine, 2,6-lutidine, etc.).

Hereinafter, the compounds of the formula (I) and the salts thereof are simply referred to as "the compound (I)".

The compound (I) of the present invention can be produced, for example, according to the process of the Scheme-I:

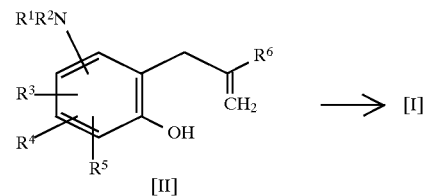

-continued
Scheme-I

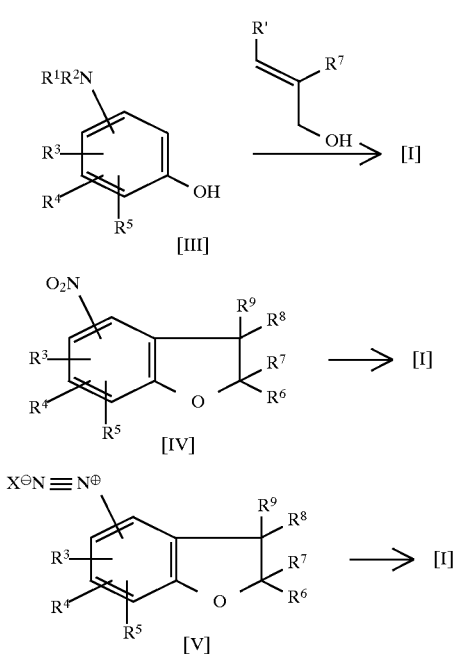

wherein $R^1$, $R^2$, $R^3$, $R^4$, $R^5$, $R^6$, $R^7$, $R^8$ and $R^9$ are as defined above, —$CH_2R'$ corresponds to $R^6$ as defined above and X is a halogen, $HSO_4$ or $NO_3$. The residue R'—C= is converted into $R^6$ by the above reaction with the compound (III). Namely, R' is a residue which constitutes the residue $R^6$ together with —$CH_2$—. Examples of the halogen represented by X are chlorine, bromine and the like.

That is, the compound (I) can be produced by cyclizing the compound (II), preferably in the presence of (1) an acid, (2) a halogen molecule, if desired, together with a base, or (3) a peracid, if desired, together with a base. The resulting product is optionally subjected to deprotecting reaction, acylating reaction, hydrogenating reaction, oxidation, carbon chain extension with Wittig reaction or substituent exchanging reaction or a combination of two or more of these reactions. The compound (I) can also be produced by condensation between the phenol (III) and an allyl alcohol derivative, preferably in the presence of a suitable acid catalyst or by reduction of the nitro compound (IV) or the diazo compound (V), and the resulting product can be optionally subjected to deprotecting reaction, acylating reaction or alkylating reaction or a combination of two or more of these reactions.

The ring closure reaction by an acid is carried out in an aqueous solution of a protic acid such as hydrochloric acid, hydrobromic acid or the like at room temperature to 150° C., or the reaction is carried out in hydrogen chloride gas, boron trifluoride etherate ($BF_3.Et_2O$) or the like in a suitable organic solvent (e.g., chloroform, toluene, etc.), preferably at a temperature in the range of −5° C. to 150° C.

The ring closure reaction by halogen is carried out by reacting the compound (II) or a salt thereof with bromine or the like, preferably in an organic solvent such as carbon halide (e.g., chloroform, methylene chloride, etc.), acetic acid or the like, if desired, in the presence of a base such as sodium acetate, triethylamine or the like at −5° C. to 100° C.

The ring closure reaction by a peracid is carried out by using a peracid such as m-chloroperbenzoic acid or the like in an organic solvent such as methylene chloride, if desired, in the presence of a base such as triethylamine at −10° to 50° C.

Friedel-Crafts reaction between the phenol derivative and the allyl alcohol derivative is carried out in an organic solvent such as dichloroethane in the presence of sulfuric acid, trifluoromethanesulfonic acid or boron trifluoride etherate, preferably at a temperature in the range of 0° to 150° C.

The reduction of the nitro compound is carried out by catalytic hydrogenation using palladium carbon as a catalyst, by using a metal such as iron, zinc, tin or the like in the presence of an acid (e.g., hydrochloric acid, acetic acid, etc.) or base (e.g., sodium hydroxide, etc.) or by using titanium trichloride in the presence of an acid (e.g., acetic acid, etc.). The reduction of the diazo compound can be carried out by similar catalytic hydrogenation or a reducing agent such as sodium hydrosulfite in water or an organic solvent at 0° to 100° C.

The oxidation after the above ring closure reaction is carried out by using the oxidizing agent obtained from dimethyl sulfoxide and oxalyl chloride or an oxidizing agent such as chromium trioxide or the like, optionally in the presence of a base such as triethylamine, in an organic solvent such as acetone at −78° C. to 25° C.

The addition-elimination reaction (Wittig reaction) is carried out using sodium hydride, sodium hydroxide, sodium alkolate, n-butyllithium, lithium diisopropylamide or the like as a base in a solvent such as dimethylformamide, tetrahydrofuran, dimethoxyethane or the like. The reaction temperature is preferably −78° C. to 80° C. and the reaction time is about 0.5 to 24 hours.

In hydrogenation of the double bond, the desired product can be obtained by using a catalyst such as palladium-carbon according to a conventional method.

The deprotection (hydrolysis) of the protected hydroxyl group can be carried out under conventional conditions of ester hydrolysis. When the product is unstable to oxygen under basic conditions, the reaction can be carried out in an atmosphere of argon to obtain the desired hydrolysate in high yield.

The acylation can be carried out by using the desired acylating agent (acid anhydride, acid halide or the like), if desired, in the presence of a base catalyst (preferably, sodium hydride, potassium carbonate, pyridine, triethylamine or the like) or an acid catalyst (e.g., sulfuric acid, hydrochloric-acid or the like) in an organic solvent (e.g., dimethylformamide, acetone, tetrahydrofuran). The reaction temperature is about −10° C. to 100° C. and the reaction time is about 10 minutes to 15 hours.

For carrying out the substituent exchanging reaction, for example, a 2-halomethyl-2,3-dihydrobenzofuran derivative cyclized by a halogen is reacted with an amine, thiol, alcohol or the like without using any solvent or in an organic solvent such as dimethylformamide, toluene or the like, if desired, in the presence of a base (e.g., sodium hydride, etc.) at a temperature in the range of −5° C. to 200° C. If desired, an autoclave is used as a reactor.

Examples of the alkylating reaction include alkylation of an amino group or a hydroxyl group and the like. For the alkylation, there can be used a halogenated alkyl (examples of the halogen are chlorine, bromine and iodine), alkyl esters of sulfuric acid or sulfonic acid, alkyl esters of phosphorous acid and the like. Normally, the alkylating agent is used in equal or twice amount and the reaction is carried out in the presence of an inorganic base (e.g., sodium hydroxide, potassium hydroxide, sodium carbonate, potassium carbonate, etc.) or an organic base (e.g., triethylamine, pyridine, etc.). The solvent used in this reaction is not limited to a specific one and an organic solvent such as tetrahydrofuran, dioxane, dimethylformamide, dimethylacetamide or the like or water can be used. The reaction is normally carried out at a temperature in the range from room temperature to 100° C.

The starting compounds (II), (III), (IV) and (V) can be synthesized by a known method (e.g., International Publication WO86/05781), a per se known method or Reference Examples as described hereinafter.

The compound (I) thus obtained can be isolated by conventional separation and purification techniques, for example, extraction, chromatography, recrystallization and the like.

When the compound (I) exists as diastereomers, each diastereomer can be optionally isolated by the above separation and purification techniques.

When the compound (I) is optically active, each of the d-isomer and l-isomer can be separated by the conventional optical resolution.

The compound (I) of the present invention has circulatory system improvement activities and antiallergic activities such as improvement of metabolism of poly unsaturated fatty acids (e.g., linolic acid, γ-linolenic acid, α-linolenic acid, arachidonic acid, dihomo-γ-linolenic acid, eicosapentaenoic acid), particularly, inhibitory activity for lipoperoxide formation reaction (antioxidation activity); inhibitory activity for formation of 5-lipoxygenase metabolite [e.g., leukotrienes, 5-hydroperoxyeicosatetraenoic acid (HPETE), 5-hydroxyeicosatetraenoic acid (HETE), lipoxins, leukotoxines, etc.]; inhibition activity for thromboxane $A_2$-synthetase; activity for maintaining and enhancing prostaglandin $I_2$-synthetase; $LTD_4$ receptor antagonism; scavenging activity for active oxygen species and the like.

Among these activities, the compound (I) of the present invention particularly tends to remarkably show lipoperoxide formation inhibitory activity (antioxidation activity).

The compound (I) has low toxicity and little side effect.

Accordingly, the compound (I) of the present invention has therapeutic and preventive effects on various diseases of mammal (e.g., mouse, rat, rabbit, dog, monkey, human, etc.) such as thrombosis due to platelet aggregation; ischemic diseases due to constriction of arterial vascular smooth muscle or vasospasm in the heart, lung, brain and kidney (e.g., cardiac infarction, cerebral apoplexy, etc.); neuropathy (e.g., Parkinson's disease, Arzheimer's disease, Lou-Gehring's disease, muscular dystrophy, etc.); functional disorders caused by central damage such as cranial injury, spinal injury, etc.; dysmnesia or emotional disturbance (disorders accompanied by nerve cell necrosis caused by hypoxia, cerebral lesion, cerebral hemorrhage, cerebral infarction, cerebral thrombosis, etc.); convulsion and epilepsia caused after cerebral apoplexy, cerebral infarction, cerebral surgery or cranial injury; nephritis; pulmonary insufficiency; bronchial asthma; inflammation; arterial sclerosis; atherosclerosis; hepatitis; acute hepatitis; cirrhosis; hypersensitivity pneumonitis; immune deficiency syndrome; circulatory diseases caused by injury of enzymes, tissue, cells, etc. of the living body due to active oxygen species (e.g., superoxide, hydroxide radical, etc.) (e.g., cardiac infarction, cerebral apoplexy, cerebral edema, nephritis, etc.); tissue fibroplastic phenomenon; carcinogenesis and the like. For example, the compound (I) of the present invention is useful as a medicinal such as an antithrombotic drug, an antivasoconstriction drug, an antiasthmatic drug, an antiallergic drug, a drug for improving circulatory system such as the heart and brain, a drug for treating nephritis, a drug for treating hepatitis, a drug for inhibiting tissue fibroplastic, a drug for scavenging active oxygen species, a drug for regulating and improving arachidonate cascade substances and the like.

The compound (I) can be orally or parenterally administered in safely as it is, or in the form of pharmaceutical compositions (e.g., tablets, capsules, solutions, injection preparations, suppositories) combined with known pharmaceutically acceptable carriers, excipient and the like. The dose varies depending upon a particular subject, administration route, conditions of diseases and the like. For example, in the case of administering orally to an adult patient with circulatory diseases, it is advantageous that the compound of the present invention is normally administered 1 to 3 times per day with a dose of about 0.1 mg/kg to 20 mg/kg body weight, preferably, 0.2 mg/kg to 10 mg/kg body weight.

The following Examples, Reference Examples and Experiments further illustrate the present invention in detail but are not to be construed to limit the scope thereof.

EXAMPLE 1

5-Amino-2-benzyl-2,4,6,7-tetramethyl-2,3-dihydrobenzofuran

Sulfuric acid (15 ml) was added to a solution of 4-amino-2,3,5-trimethylphenol (20.0 g, 0.13 mol) and 2-methyl-3-phenyl-2-propenol (25.0 g, 0.17 mol) in dichloromethane (100 ml) and the mixture was heated under reflux for 1 hour. The resulting reaction mixture was neutralized with aqueous saturated sodium bicarbonate solution and the product was extracted with ethyl acetate. The extract was washed with water and dried and then the solvent was distilled off. The residue was purified by silica gel column chromatography (isopropyl ether) and crystallized from hexane to obtain the desired compound (7.2 g, yield: 19.3%), m.p. 68°–69° C.

NMR (CDCl$_3$) δ1.38 (3H, s), 2.06 (3H, s), 2.10 (3H, s), 2.16 (3H, s), 2.80 (2H, broad s), 2.85 (2H, d, J=13.6 Hz), 3.08 (2H, d, J=13.6 Hz), 7.26 (5H, m).

EXAMPLE 2

5-Amino-2,2,4,6,7-pentamethyl-2,3-dihydrobenzofuran hydrochloride

4-Amino-2,3,5-trimethylphenol (2.0 g, 13.2 mmol) and 2-methyl-2-propenol (1.15 g, 15.8 g) were heated under reflux in dichloromethane (20 ml) together with sulfuric acid (2 ml) for 18 hours. The reaction mixture was washed with aqueous saturated sodium bicarbonate solution, dried and then concentrated. The residue was purified by silica gel column chromatography (isopropyl ether). The purified product was converted into its hydrochloride and it was crystallized from ethanol-isopropyl ether to obtain the desired compound (460 mg, yield: 14.4%), m.p. 248°–250° C.

NMR (DMSO-d$_6$) δ1.47 (6H, s), 2.08 (3H, s), 2.18 (6H, s), 3.03 (2H, s), 9.80 (2H, broad s).

EXAMPLE 3

5-Amino-2,2,4,6,7-pentamethyl-2,3-dihydrobenzofuran hydrochloride

4-Formylamino2,3,5-trimethyl-1-(2-methyl-2-propenyloxy)benzene (7.33 g, 35.7mmol) was dissolved in methanol (100 ml) and to the solution was added conc. hydrochloric acid (30 ml) with ice-cooling. After the atmosphere in the flask was displaced with argon, the mixture was heated under reflux for 2 hours. The reaction mixture was cooled, then neutralized with aqueous sodium bicarbonate solution and extracted with chloroform. The extract was washed with water and then concentrated under reduced pressure. The residue was crystallized from isopropyl ether to obtain the desired compound (6.40 g, yield: 99.2%). A part of the compound was converted into its hydrochloride and then crystallized from methanol, m.p. 248°–250° C. (dec.).

NMR (DMSO-$d_6$) δ1.41 (6H, s), 2.02 (3H, s), 2.20 (6H, s), 9.65 (2H, broad s).

EXAMPLE 4

5-Amino-2,2,4,6-tetramethyl-7-(2-methyl-1-propenyl)-2,3-dihydrobenzofuran hydrochloride According to the same manner as that described above, the title compound was synthesized (yield: 80.1%), m.p. 207°–208° C. (dec.).

NMR (DMSO-$d_6$) δ1.39 (6H, s), 1.46 (3H, s), 1.86 (3H, s), 2.13 (3H, s), 2.21 (3H, s), 2.97 (2H, s), 5.90 (1H, s), 9.38 (2H, broad s).

EXAMPLE 5

5-Acetylamino-2,2,6,7-tetramethyl-4-nitro-2,3-dihydrobenzofuran

The title compound was synthesized according to the same manner as that described in Reference Example 48 hereinafter (yield: 89.4%), m.p. 203° C. (dichloromethane-isopropyl ether).

NMR (CDCl$_3$) δ1.48 (6H, s), 2.15 (3H, s), 2.18 (3H, s), 2.19 (3H, s), 3.29 (2H, s), 7.79 (1H, broad s).

EXAMPLE 6

5-Acetylamino-2,2,4,7-tetramethyl-6-nitro-2,3-dihydrobenzofuran

The title compound was synthesized according to the same manner as that described above (yield: 77.6%), m.p. 203°–204° C. (dichloromethane-isopropyl ether).

NMR (CDCl$_3$) δ1.50 (6H, s), 2.09 (3H, s), 2.12 (3H, s), 2.14 (3H, s), 3.00 (2H, s), 7.09 (1H, s).

EXAMPLE 7

7-Amino-2,2,4,5,6-pentamethyl-2,3-dihydrobenzofuran hydrochloride 2,2,4,5,6-Pentamethyl-7-nitro-2,3-dihydrobenzofuran (310 mg, 1.3 mmol) was dissolved in ethanol (10 ml) and the solution was subjected to catalytic reduction using 5% palladium carbon (0.6 g) as a catalyst. After the catalyst was filtered off, the filtrate was concentrated. The residue was purified by column chromatography on silica gel (hexane-isopropyl ether, 7:3), converted into its hydrochloride and then crystallized from ethanol-isopropyl ether to obtain the desired compound (170 mg, yield: 53.3%), m.p. 207°–212° C.

NMR (DMSO-$d_6$) δ1.47 (6H, s), 2.08 (3H, s), 2.12 (3H, s), 2.18 (3H, s), 3.03 (2H, s), 9.80 (2H, broad s).

EXAMPLE 8

5-Amino-2,2,4,6,7-pentamethyl-3-phenyl-2,3-dihydrobenzofuran 2,2,4,6,7-Pentamethyl-5-nitro-3-phenyl-2,3-dihydrobenzofuran (2.0 g, 6.4 mmol) was dissolved in ethanol (15 ml) and the solution was subjected to catalytic reduction using 5% palladium carbon (2.0 g) as a catalyst. After the catalyst was filtered off, the filtrate was concentrated. The residue was purified by column chromatography on silica gel (isopropyl ether) and then crystallized from hexane to obtain the desired compound (1.33 g, yield: 73.6%), m.p. 131°–132° C.

NMR (CDCl$_3$) δ1.00 (3H, s), 1.48 (3H, s), 1.77 (3H, s), 2.12 (3H, s), 2.19 (3H, s), 3.10 (2H, broad s), 4.11 (1H, s), 6.95 (2H, m), 7.20 (3H, m).

EXAMPLE 9

5-Amino-3-(4-fluorophenyl)-2,2,4,6,7-pentamethyl-2,3-dihydrobenzofuran

The title compound was synthesized according to the same manner as that described above (yield: 70.2%), m.p. 126°–127° C. (hexane).

NMR (CDCl$_3$) δ0.99 (3H, s), 1.47 (3H, s), 1.77 (3H, s), 2.12 (3H, s), 2.18 (3H, s), 3.10 (2H, broad s), 4.09 (1H, s), 6.93 (4H, m).

EXAMPLE 10

5-Amino-3-(4-isopropylphenyl)-2,2,4,6,7-pentamethyl-2,3-dihydrobenzofuran

The title compound was synthesized according to the same manner as that described above (yield: 85.0%), m.p. 134°–135° C. (hexane).

NMR (CDCl$_3$) δ1.00 (3H, s), 1.22 (6H, d, J=6.8 Hz), 1.47 (3H, s), 1.78 (3H, s), 2.13 (3H, s), 2.19 (3H, s), 2.85 (1H, septet, J=6.8 Hz), 3.10 (2H, broad s), 4.08 (1H, s), 6.85 (2H, m), 7.07 (2H, d, J=8.0 Hz).

EXAMPLE 11

5-Amino-2,2,4,6,7-pentamethyl-3-(3-pyridyl)-2,3-dihydrobenzofuran

The title compound was synthesized according to the same manner as that described above (yield: 53.8%), m.p. 130°–131° C. (hexane).

NMR (CDCl$_3$) δ1.02 (3H, s), 1.50 (3H, s), 1.77 (3H, s), 2.12 (3H, s), 2.19 (3H, s), 3.04 (2H, broad s), 4.12 (1H, s), 7.16 (2H, m), 8.36 (1H, m), 8.46 (1H, t, J=3.2 Hz).

EXAMPLE 12

5-Amino-3-(3-amino-4-dimethylaminophenyl)-2,2,4,6,7-pentamethyl-2,3-dihydrobenzofuran dihydrochloride The title compound was synthesized as an amorphous product according to the same manner as that described above (yield: 42.4%).

NMR (DMSO-$d_6$) δ1.04 (3H, s), 1.44 (3H, s), 1.99 (3H, s), 2.13 (3H, s), 2.29 (3H, s), 3.02 (6H, s), 4.24 (1H, s), 6.00–7.50 (5H, m), 9.85 (2H, broad s).

EXAMPLE 13

5-Amino-3-isopropyl-2,2,4,6,7-pentamethyl-2,3-dihydrobenzofuran hydrochloride

The title compound was synthesized according to the same manner as that described above (yield: 76.6%), m.p. 225°–230° C. (ethanol).

NMR (DMSO-$d_6$) δ0.70 (3H, d, J=6.6 Hz), 0.96 (3H, d, J=6.6 Hz), 1.21 (3H, s), 1.57 (3H, s), 1.62 (1H, m), 2.09 (3H, s), 2.53 (3H, s), 2.57 (3H, s), 2.76 (1H, d, J=2.8 Hz), 10.07 (2H, broad s).

EXAMPLE 14

4,5-Diamino-2,2,6,7-tetramethyl-2,3-dihydrobenzofuran hydrochloride

The title compound was synthesized according to the same manner as that described above (yield: 96.9%), m.p. 248°–251° C. (ethanol).

NMR (DMSO-$d_6$) δ1.39 (6H, s), 1.93 (3H, s), 2.09 (3H, s), 2.82 (2H, s), 3.36 (4H, broad s).

EXAMPLE 15

5-Acethylamino-6-amino-2,2,4,7-tetramethyl-2,3-dihydrobenzofuran

The title compound was synthesized according to the same manner as that described above (yield: 98.7%), m.p. 155°–157° C. (isopropyl ether).

NMR (CDCl$_3$) δ1.44 (6H, s), 1.82 and 2.23 (3H, s), 2.00–2.05 (6H, m), 2.87 (2H, s), 3.75 (2H, broad s), 6.40 and 6.62 (1H, broad s).

EXAMPLE 16

5-Acethylamino-4-amino-2,2,6,7-tetramethyl-2,3-dihydrobenzofuran

The title compound was synthesized according to the same manner as that described above (yield: 91.4%), m.p. 172–173 (ethanol-ether).

NMR (CDCl$_3$) δ1.46 (6H, s), 1.83 and 2.23 (3H, s), 2.05–2.09 (6H, m), 2.83 (2H, s).

EXAMPLE 17

5-Amino-2,2,4,6,7-pentamethyl-3-(4-methylphenyl)-2,3-dihydrobenzofuran 2,2,4,6,7-Pentamethyl-3-(4-methylphenyl)-5-nitro-2,3-dihydrobenzofuran (1.26 9, 3.9 mmol) was dissolved in methanol (30 ml). Zinc powder (1.3 9) and 1N sodium hydroxide (15 ml) were added to the solution and the mixture was heated under reflux for 3 hours. Insoluble materials were filtered off and water was added. The mixture was extracted with ethyl acetate. The extract was washed with water, dried and then the solvent was distilled off. The residue was purified by column chromatography on silica gel (hexane-isopropyl ether, 95:5) and crystallized from hexane to obtain the desired compound (710 mg, yield: 53.7%), m.p. 119°–120° C.

NMR (CDCl$_3$) δ1.00 (3H, s), 1.47 (3H, s), 1.78 (3H, s), 2.13 (3H, s), 2.20 (3H, s), 2.31 (3H, s), 3.20 (2H, broad s), 4.09 (1H, s), 6.82. (2H, m), 7.10 (2H, m).

EXAMPLE 18

5-Amino-2,2,4,6,7-pentamethyl-3-(4-propylphenyl)-2,3-dihydrobenzofuran

The title compound was synthesized according to the same manner as that described above (yield: 65.6%), m.p. 68°–69° C. (methanol).

NMR (CDCl$_3$) δ0.90 (3H, t, J=7.2 Hz), 0.99 (3H, s), 1.47 (3H, s), 1.60 (2H, sextet, J=7.2 Hz), 1.77 (3H, s), 2.12 (3H, s), 2.19 (3H, s), 2.54 (2H, t, J=7.2 Hz), 3.10 (2H, broad s), 4.09 (1H, s), 6.82 (2H, m), 7.03 (2H, d, J=8.0 Hz).

EXAMPLE 19

5-Amino-2,2,4,6,7-pentamethyl-3-(4-pentylphenyl)-2,3-dihydrobenzofuran

The title compound was synthesized according to the same manner as that described above (yield: 55.6%), m.p. 67°–68° C. (methanol).

NMR (CDCl$_3$) δ0.87 (3H, t, J=6.6 Hz), 1.00 (3H, s), 1.31 (4H, m), 1.47 (3H, s), 1.58 (2H, m), 1.78 (3H, s), 2.12 (3H, s), 2.19 (3H, s), 2.55 (2H, t, J=7.2 Hz), 3.20 (2H, broad s), 4.09 (1H, s), 6.82 (2H, m), 7.03 (2H, d, J=8.0 Hz).

EXAMPLE 20

5-Amino-2,4,6,7-tetramethyl-2-piperidinomethyl-2,3-dihydrobenzofuran

The title compound was synthesized according to the same manner as that described above (yield: 82.1%), m.p. 60°–61° C. (isopropyl ether).

NMR (CDCl$_3$) δ1.30–1.60 (6H, m), 1.42 (3H, s), 2.07 (6H, s), 2.10 (3H, s), 2.35–2.65 (6H, m), 2.80 (1H, d, J=15.9 Hz), 3.10 (2H, broad s), 3.11 (1H, d, J=15.9 Hz).

EXAMPLE 21

5-Amino-2,4,6,7-tetramethyl-2-morpholinomethyl-2,3-dihydrobenzofuran

The title compound was synthesized according to the same manner as that described above (yield: 38.0%), m.p. 114°–115° C. (isopropyl ether).

NMR (CDCl$_3$) δ1.42 (3H, s), 2.07 (9H, s), 2.40–2.70 (6H, m), 2.81 (1H, d, J=15.0 Hz), 3.13 (1H, d, J=15.0 Hz), 3.20 (2H, broad s), 3.67 (4H, t, J=4.6 Hz).

EXAMPLE 22

5-Amino-2,4,6,7-tetramethyl-2-[2-(dimethylamino)-ethyl]-2,3-dihydrobenzofuran dihydrochloride The title compound was synthesized according to the same manner as that described above (yield: 46.5% ), m.p. 200°–203° C. (dec.) (ethanol-isopropyl ether).

NMR (DMSO-$d_6$) δ1.41 (3H, s), 2.06 (3H, s), 2.17 (2H, m), 2.22 (3H, s), 2.24 (3H, s), 2.74 (6H, s), 2.96 (1H, d, J=16.0 Hz), 3.11 (2H, m), 3.16 (1H, d, J=16.0 Hz), 9.78 (2H, broad s).

EXAMPLE 23

5-Amino-2,4,6,7-tetramethyl-2-(2-piperidinoethyl)-2,3-dihydrobenzofuran dihydrochloride The title compound was synthesized according to the same manner as that described above (yield: 41.9%), m.p. 260°–270° C. (dec.) (ethanol-isopropyl ether).

NMR (DMSO-$d_6$) δ1.41 (3H, s), 1.76 (6H, m), 2.06 (3H, s), 2.22 (3H, s), 2.23 (3H, s), 2.23 (2H, m), 2.84 (4H, m), 2.95 (1H, d, J=15.8 Hz), 3.05 (2H, m), 3.15 (1H, d, J=15.8 Hz), 9.65 (2H, broad s).

EXAMPLE 24

5-Amino-2,2,4,6-tetramethyl-7-(dimethylamino)-methyl-2,3-dihydrobenzofuran oxalate Aqueous 50% dimethylamine solution (6.46 ml, 64.2 mmol) was added dropwise to a suspension of paraformaldehyde (1.61 g, 42.8 mmol) in ethanol (10 ml). The mixture was stirred at room temperature until the mixture became homogeneous (for 30 minutes). This solution was added dropwise to a solution of 4-acethylamino-3,5-dimethyl-2-(2-methyl- 2-propenyl)phenol (4.98 g, 21.4 mmol) in ethanol (30 ml). The resulting mixture was heated under reflux for 3.5 hours under an argon atmosphere. The reaction mixture was cooled and then concentrated under reduced pressure. The residue was purified by column chromatography on silica gel (chloroform-methanol, 95:5) to obtain the desired compound (5.45 g, yield: 87.7%) as brown oil.

This was dissolved in methanol (60 ml) and conc. hydrochloric acid (20 ml) was added. The mixture was heated under reflux for 1.5 hours under an argon atmosphere. After the reaction mixture was cooled, excess aqueous sodium bicarbonate solution was added and the mixture was extracted with chloroform. The extract was washed with water, dried and concentrated. The residue was purified by column chromatography on silica gel (chloroform-methanol, 88:12) to obtain the desired compound (4.86 9, yield: 90.5%) as brown oil.

This was dissolved in ethanol (3 ml) and 5N sodium hydroxide was added to the solution. The mixture was stirred for 13 hours at 200° C. in a sealed tube under an argon atmosphere. After the reaction mixture was cooled, water was added and the mixture was extracted with chloroform. The extract was washed with water, dried and then concentrated. The residue was purified by column chromatography on silica gel (chloroform-methanol, 88:12) to obtain the product (1.70 g, yield: 41.5%). A part of the product was converted into its oxalate salt and then recrystallized from ethanol to obtain the desired compound, m.p. 178°–180° C. (ethanol).

NMR (DMSO-$d_6$) δ1.39 (6H, s), 2.02 (3H, s), 2.07 (3H, s), 2.74 (6H, s), 2.93 (2H, s), 4.13 (2H, s), 4.52 (4H, broad s).

EXAMPLE 25

5-Amino-2,2,4,6-tetramethyl-7-piperidinomethyl-2,3-dihydrobenzofuran oxalate

The title compound was synthesized according to the same manner as that described above (yield: 47.9%–41.0%–55.7%), m.p. 110°–112° C. (ethanol).

NMR (DMSO-$d_6$) δ1.44 (6H, s), 1.62–1.80 (6H, m), 2.01 (3H, s), 2.03 (3H, s), 2.99 (2H, s), 3.11 (4H, broad s), 4.09 (2H, s), 4.48 (4H, broad s).

EXAMPLE 26

5-Amino-2,2,4,6-tetramethyl-7-morpholinomethyl-2,3-dihydrobenzofuran oxalate

The title compound was synthesized according to the same manner as that described above (yield: 55.1%–77.3%–55.2%), m.p. 118°–120° C. (ethanol).

NMR (DMSO-$d_6$) δ1.38 (6H, s), 2.01 (3H, s), 2.08 (3H, s), 2.85 (4H, broad s), 2.90 (2H, s), 3.68 (4H, broad s), 3.83 (2H, s), 5.03 (4H, broad s).

EXAMPLE 27

5-Acetylamino-2-hydroxymethyl-2,4,6,7-tetramethyl- 2,3-dihydrobenzofuran

4-Acethylamino-2,3,5-trimethyl-6-(2-methyl-2-propenyl)phenol (2.0 g, 8.1 mmol) was dissolved in dichloromethane (20 ml). m-Chloroperbezoic acid (70% purity, 2.2 g, 8.9 mmol) was added slowly to the solution with stirring under ice cooling. After the addition was completed, the reaction mixture was stirred at room temperature for 1 hour and triethylamine (2 ml) was added. The reaction mixture was washed with water, dried and then concentrated. The residue was purified by column chromatography on silica gel (ethyl acetate) to obtain the desired compound (1.1 g, yield: 51.7% yield) as oil.

NMR (CDCl$_3$) δ1.43 (3H, s), 1.96 (1H, m), 2.07 (3H, s), 2.09 (6H, s), 2.20 (3H, s), 2.81 (1H, d, J=15.4 Hz), 3.16 (1H, d, J=15.4 Hz), 3.63 (2H, m), 6.66 (1H, broad s).

EXAMPLE 28

5-Formylamino-2-hydroxymethyl-2,4,6,7-tetramethyl-2,3-dihydrobenzofuran

The title compound was synthesized according to the same manner as that described above (yield: 59.9%), m.p. 149°–150° C. (ethyl acetate-hexane).

NMR (DMSO-$d_6$) δ1.33 (3H, s), 1.97 (3H, s), 1.98 (3H, s), 2.00 (3H, s), 2.73 (1H, d, J=15.4 Hz), 3.13 (1H, d, J=15.4 Hz), 3.42 (2H, d, J=5.8 Hz), 5.01 (1H, t, J=5.8 Hz), 7.83 (0.2H, d, J=11.6 Hz), 8.21 (0.8H, d, J=1.2H), 9.05 (0.2H, d, J=11.6 Hz), 9.20 (0.8H, broad s).

EXAMPLE 29

2-Bromomethyl-5-formylamino-2,4,6,7-tetramethyl-2,3-dihydrobenzofuran

4-Formylamino-2,3,5-trimethyl-6-(2-methyl-2-propenyl)phenol (50 g, 0.21 mol) and sodium acetate (30.5 g, 0.37 mol) were added to acetic acid (500 ml). Bromine (16.5 ml, 0.21 mol) was added dropwise to the mixture with stirring. After the reaction mixture was stirred for 30 minutes, the mixture was poured into ice water and the product was extracted with ethyl acetate. The extract was washed with aqueous saturated sodium bicarbonate solution, dried and then concentrated. The residue was dissolved in ethyl acetate again and insoluble materials were filtered off. The filtrate was concentrated and isopropyl ether was added to the residue. The crystals precipitated were filtered off to obtain the desired compound (44.0 g, yield: 65.7%), m.p. 157°–158° C.

NMR (CDCl$_3$) δ1.61 (1.5H, s), 1.63 (1.5H, s), 2.09 (3H, s), 2.11 (3H, s), 2.13 (1.5H, s), 2.16 (1.5H, s), 2.93 (1H, d, J=15.8 Hz), 3.28 (0.5H, d, J=15.8 Hz), 3.29 (0.5H, d, J=15.8 Hz), 3.51 (1H, s), 3.53 (1H, s), 6.77 (0.5H, broad s), 6.85 (0.5H, d, J=12.0 Hz), 7.96 (0.5H, d, J=12.0 Hz), 8.40 (0.5H, d, J=1.4 Hz).

EXAMPLE 30

5-Acetylamino-2-formyl-2,4,6,7-tetramethyl-2,3-dihydrobenzofuran

A solution of oxalyl chloride (0.45 ml, 4.7 mmol) in dichloromethane (10 ml) was cooled to −78° C. and dimethyl sulfoxide (1 ml) was added dropwise with stirring. After stirring at the same temperature for 2 hours, a solution of 5-acetylamino-2-hydroxymethyl-2,4,6,7-tetramethyl-2,3-dihydrobenzofuran (1.1 g, 4.2 mmol) in dichloromethane (5 ml) was added dropwise and the mixture was stirred for additional 30 minutes. Triethylamine (3.5 ml) was added and the mixture was stirred for 10 minutes. The reaction mixture was washed with 1N hydrochloric acid and aqueous saturated sodium bicarbonate solution. The reaction mixture was dried and then concentrated. The residue was purified by column chromatography on silica gel (ethyl acetate) to obtain the desired compound (0.47 g, yield: 43.1%) as oil.

NMR (CDCl$_3$) δ1.55 (3H, s), 2.06 (3H, s), 2.11 (3H, s), 2.13 (3H, s), 2.21 (3H, s), 2.94 (1H, d, J=15.8 Hz), 3.41 (1H, d, J=15.8 Hz), 6.72 (1H, broad s).

EXAMPLE 31

2-Formyl-5-formylamino-2,4,6,7-tetramethyl-2,3-dihydrobenzofuran

The title compound was synthesized as oil according to the same manner as that described above (yield: 25.5%).

NMR (CDCl$_3$) δ1.55 (1.5H, s), 1.57 (1,5H, s), 2.08 (3H, s), 2.12 (3H, s), 2.15 (3H, s), 2.94 (1H, d, J=15.4 Hz), 3.41 (0.5H, d, J=15.4 Hz), 3.44 (0.5H, d, J=15.4 Hz), 7.00 (1H, m), 7.95 (0.5H, d, J=12.0 Hz), 8.34 (0.5H, d, J=1.8 Hz), 9.73 (0.5H, s), 9.74 (0.5 Hz, s).

EXAMPLE 32

(Z)-5-Acetylamino-2,4,6,7-tetramethyl-2-styryl-2,3-dihydrobenzofuran

A suspension of benzyltriphenylphosphonium chloride (0.7 g, 1.8 mmol) in tetrahydrofuran (10 ml) was cooled to −20° C. and n-butyllithium hexane solution (1.6M, 1.12 ml, 1.8 mmol) was added dropwise. The reaction mixture was stirred for 30 minutes and then a solution of 5-acetylamino-2-formyl-2,4,6,7-tetramethyl-2,3-dihydrobenzofuran (0.45 g, 1.7 mmol) in tetrahydrofuran (5 ml) was added. The reaction mixture was stirred at room temperature for additional 30 minutes. Water was added to the reaction mixture and the product was extracted with ethyl acetate. The extract was washed with water, dried and then concentrated. The residue was purified by column chromatography on silica gel (isopropyl ether-ethyl acetate, 1:1) to obtain the desired compound (0.44 g, yield: 76.2%) as oil.

NMR (CDCl$_3$) δ1.55 (3H, s), 1.87 (3H, s), 1.98 (3H, s), 2.05 (3H, s), 2.19 (3H, s), 2.94 (1H, d, J=15.4 Hz), 3.19 (1H, d, J=15.4 Hz), 5.92 (1H, d, J=12.8 Hz), 6.50 (1H, d, J=12.8 Hz), 6.62 (1H, broad s), 7.25 (5H, m).

EXAMPLE 33

(Z)-5-Acetylamino-2,4,6,7-tetramethyl-2-[2-(4-fluorophenyl) ethenyl]-2,3-dihydrobenzofuran The title compound was synthesized as oil according to the same manner as that described above (yield: 81.3%).

NMR (CDCl$_3$) δ1.55 (3H, s), 1.84 (3H, s), 2.00 (3H, s), 2.05 (3H, s), 2.19 (3H, s), 2.95 (1H, d, J=14.0 Hz), 3.19 (1H, d, J=14.0 Hz), 5.88 (1H, d, J=12.6 Hz), 6.45 (1H, d, J=12.6 Hz), 6.69 (1H, broad s), 7.00 (2H, m), 7.26 (2H, m).

EXAMPLE 34

Ethyl 3-[5-formylamino-2,4,6,7-tetramethyl-2,3-dihydrobenzofuran-2-yl]acrylate

2-Formyl-5-formylamino-2,4,6,7-tetramethyl-2,3-dihydrobenzofuran (1.0 g, 4.1 mmol), triethylphosphonoacetate (0.91 g, 4.1 mmol) and sodium hydride (60% purity, 162 mg, 4.1 mmol) were added to dimethylformamide and the mixture was stirred at room temperature for 1 hour. The reaction mixture was diluted with water and the product was extracted with ethyl acetate. The extract was washed with water and dried and then the solvent was distilled off. The residue was purified by column chromatography on silica gel (ethyl acetate-isopropyl ether, 1:1) to obtain the desired compound (0.5 g, yield: 39.0%) as oil.

NMR (CDCl$_3$) δ1.29 (3H, t, J=7.2 Hz), 1.60 (3H, s), 2.06 (1.5H, s), 2.11 (1.5H, s), 2.13 (1.5H, s), 2.15 (1.5H, s), 2.17 (3H, s), 3.05 (1H, d, J=15.4 Hz), 3.15 (1H, d, J=15.4 Hz), 4.19 (2H, d, J=7.2 Hz), 6.02 (1H, d, J=15.6 Hz), 6.92 (0.5H, broad s), 6.95 (0.5H, d, J=12.0 Hz), 7.02 (1H, d, J=15.6 Hz), 7.95 (0.5H, d, J=12.0 Hz), 8.39 (0.5H, d, J=1.6 Hz).

EXAMPLE 35

5-Acethylamino-2,4,6,7-tetramethyl-2-(2-phenylethyl)-2,3-dihydrobenzofuran

5% Palladium carbon (0.3 g) was added to a solution of (Z)-5-acetylamino-2,4,6,7-tetramethyl-2-styryl-2,3-dihydrobenzofuran (1.0 g, 3.0 mmol) in ethanol and the mixture was stirred for 1 hour under a hydrogen atmosphere. The catalyst was filtered off and then the filtrate was concentrated. The residue was purified by column chromatography on silica gel (isopropyl ether-ethyl acetate, 1:1) to obtain the desired compound (0.95 g, yield: 94.4%) as oil.

NMR (CDCl$_3$) δ1.48 (3H, s), 2.02 (2H, m), 2.05 (3H, s), 2.09 (3H, s), 2.14 (3H, s), 2.22 (3H, s), 2.72 (2H, m), 2.89 (1H, d, J=15.4 Hz), 3.05 (1H, d, J=15.4 Hz), 7.10–7.30 (5H, m), 7.15 ((1H, broad s).

EXAMPLE 36

5-Acetylamino-2-[2-(4-fluorophenyl) ethyl]-2,4,6,7-tetramethyl-2,3-dihydrobenzofuran The title compound was synthesized as oil according to the same manner as that described above (yield: 90.3%)

NMR (CDCl$_3$) δ1.47 (3H, s), 1.98 (2H, m), 2.06 (3H, s), 2.10 (6H, s), 2.20 (3H, s), 2.69 (2H, m), 2.90 (1H, d, J=15.4 Hz), 3.05 (1H, d, J=15.4 Hz), 6.70 (1H, broad s), 6.95 (2H, m), 7.13 (2H, m).

EXAMPLE 37

5-Amino-7-(2-methylpropyl)-2,2,4,6-tetramethyl-2,3-dihydrobenzofuran hydrochloride 10% Palladium carbon (1.0 g) was added to a solution of 5-amino-7-(2-methyl-1-propenyl)-2,2,4,6-tetramethyl-2,3-dihydrobenzofuran (1.50 g, 6.11 mmol) in ethanol (100 ml) and the mixture was heated under reflux for 3 hour under a hydrogen atmosphere. The reaction mixture was cooled and filtered and then the filtrate was concentrated. The residue was crystallized from isopropyl ether to obtain a product (1.45 g, yield: 95.9% yield. This compound was converted into its hydrochloride salt and then recrystallized from ethanol to obtain the desired compound (0.90 g, yield: 51.9% yield), m.p. 223°–225° C. ethanol).

NMR (DMSO-d$_6$) δ0.85 (6H, d, J=6.6 Hz), 1.39 (6H, s), 1.63–1.84 (1H, m), 2.21 (3H, s), 2.22 (3H, s), 2.38 (2H, d, J=7.2 Hz), 2.96 (2H, s), 9.54 (2H, broad s).

EXAMPLE 38

5-Formylamino-2,2,4,6,7-pentamethyl-2,3-dihydrobenzofuran

5-Amino-2,2,4,6,7-pentamethyl-2,3-dihydrobenzofuran (1.00 g, 4.87 mmol) was dissolved in formic acid (20 ml) and the solution was heated under reflux for 48 hours. The reaction mixture was concentrated under reduced pressure.

Saturated sodium bicarbonate solution was added to the residue and the mixture was extracted with chloroform. The extract was washed with saturated saline, dried and then concentrated under reduced pressure. The residue was purified by column chromatography on silica gel (chloroform-methanol, 97:3) to obtain the desired compound (1.06 g, yield: 93.3%). A part of it was recrystallized from dichloromethan-isopropyl ether to obtain white prisms, m.p. 177°–179° C.

NMR (CDCl$_3$) δ1.46 (3H, s), 1.48 (3H, s), 2.09–2.16 (9H, m), 2.94 (2H, s), 6.68 (1H, broad s), 7.97 (0.5H, d, J=12.0 Hz), 8.40 (0.5H, d, J=1.4 Hz).

EXAMPLE 39

5-Acetylamino-2,2,4,6,7-pentamethyl-2,3-dihydrobenzofuran

Acetyl chloride (460 mg, 5.84 mmol) was added dropwise with ice cooling to a solution of 5-amino-2,2,4,6,7-pentamethyl-2,3-dihydrobenzofuran (100 g, 4.87 mmol) and triethylamine (640 mg, 6.33 mmol) in tetrahydrofuran (20 ml). After the addition was completed, the mixture was stirred for 4 hours. Water was added to the reaction mixture and the mixture was extracted with chloroform. The extract was washed with saturated sodium bicarbonate solution and saturated saline, dried and concentrated. The residue was purified by column chromatography on silica gel (chloroform-methanol, 97:3) to obtain the desired compound (920 mg, yield: 76.4%). A part of it was recrystallized from dichloromethane-isopropyl ether, m.p. 190° C. (dichloromethane-isopropyl ether).

NMR (CDCl$_3$) δ1.46 (6H, s), 1.73 and 2.21 (3H, s), 2.06 (3H, s), 2.09 (3H, s), 2.14 (3H, s), 2.93 (2H, s), 6.63 (1H, broad s).

EXAMPLE 40

2,2,4,6,7-Pentamethyl-5-propionylamino-2,3-dihydrobenzofuran

The title compound was synthesized according to the same manner as that described above (yield: 99.8%), m.p. 146° C. (dichloromethane-isopropyl ether).

NMR (CDCl$_3$) δ1.06 and 1.31 (3H, t, J=7.4 Hz), 1.46 and 1.50 (6H, s), 1.92 and 2.44 (2H, q, J=7.4 Hz), 2.04–2.13 (9H, m), 2.93 (2H, s), 6.53 and 6.59 (1H, broad s).

EXAMPLE 41

5-Isobutyrylamino-2,2,4,6,7-pentamethyl-2,3-dihydrobenzofuran

The title compound was synthesized according to the same manner as that described above (yield: 70.8%), m.p. 136°–138° C. (dichloromethane-isopropylether).

NMR (CDCl$_3$) δ0.87 and 1.05 (3H, t, J=7.4 Hz), 1.46 and 1.51 (6H, s), 1.74–1.92 (2H, m), 2.05–2.09 (9H, m), 2.10–2.12 (2H, m), 2.39 (2H, t, J=7.4 Hz), 2.93 (2H, s), 6.52–6.62 (1H, m), 6.53 and 6.60 (1H, broad s).

EXAMPLE 42

5-Benzoylamino-2,2,4,6,7-pentamethyl-2,3-dihydrobenzofuran

The title compound was synthesized according to the same manner as that described above (yield: 84.5%), m.p. 263°–265° C. (dichloromethane-isopropyl ether).

NMR (CDCl$_3$) δ1.48 (6H, s), 2.12 (6H,s), 2.16 (3H, s), 2.96 (2H, s), 7.45–7.57 (3H, m), 7.90–7.96 (2H, m).

EXAMPLE 43

5-Isobutyrylamino-2,2,4,6,7-pentamethyl-2,3-dihydrobenzofuran

The title compound was synthesized according to the same manner as that described above (yield: 92.3%), m.p. 170°–172° C. (dichloromethane-isopropyl ether).

NMR (CDCl$_3$) δ1.30 (6H, d, J=7.0 Hz), 1.46 (6H, s), 2.03 (3H, s), 2.08 (6H, s), 2.61 (1H, septet, J=7.0 Hz), 2.92 (2H, s), 6.57 (1H, broad s).

EXAMPLE 44

5-Ethoxycarbonylamino-2,2,4,6,7-pentamethyl-2,3-dihydrobenzofuran

The title compound was synthesized according to the same manner as that described above (yield: 74.6%), m.p. 102°–104° C. (isopropyl ether-pentane).

NMR (CDCl$_3$) δ1.31 (3H, t, J=7.4 Hz), 1.45 and 1.46 (6H, s), 2.09 (6H, s), 2.13 (3H, s), 2.93 (2H, s), 4.20 (2H, q, J=7.4 Hz), 5.87 (1H, broad s).

EXAMPLE 45

5-Methanesulfonylamino-2,2,4,6,7-pentamethyl-2,3-dihydrobenzofuran

The title compound was synthesized according to the same manner as that described above (yield: 65.7%), m.p. 159°–160° C. (dichloromethane-isopropyl ether).

NMR (CDCl$_3$) δ1.47 (6H, s), 2.10 (3H, s), 2.25 (3H, s), 2.28 (3H, s), 2.93 (2H, s), 3.03 (3H, s), 5.70 (1H, s).

EXAMPLE 46

2,2,4,6,7-Pentamethyl-5-(p-toluenesulfonylamino)-2,3-dihydrobenzofuran

5-Amino-2,2,4,6,7-pentamethyl-2,3-dihydrobenzofuran 2.00 g, 9.74 mmol) and p-toluenesulfonyl chloride (2.04 g, 10.7 mmol) were dissolved in pyridine (30 ml) and stirred at 50° C. for 1 hour. The reaction mixture was concentrated under reduced pressure and the residue was dissolved in chloroform. The mixture was washed with 1N hydrochloric acid and saturated saline and dried and then the solvent was distilled off under reduced pressure. The residue was purified by column chromatography on silica gel (hexane-ethyl acetate, 97:3). The crude crystals were recrystallized from dichloromethane-isopropyl ether to obtain the desired compound (2.41 g, yield: 68.8% yield), m.p. 219°–220° C. (dichloromethane-isopropyl ether).

NMR (CDCl$_3$) δ1.46 (6H, s), 1.80 (3H, s), 1.93 (3H, s), 2.01 (3H, s), 2.43 (3H, s), 2.87 (2H, s), 5.81 (1H, s), 7.24 (2H, d, J=8.4 Hz), 7.60 (2H, d, J=8.4 Hz).

EXAMPLE 47

5-Ethylamino-2-[2-(4-fluorophenyl) ethyl]-2,4,6,7-tetramethyl-2,3-dihydrobenzofuran To tetrahydrofuran (20 ml) were added 5-acetylamino-2,4,6,7-tetramethyl-2-[2-(4-fluorophenyl) ethyl]-2,3-dihydrobenzofuran (1.2 g, 3.4 mmol) and lithium aluminum hydride. The mixture was heated under reflux for 3 hours. The reaction mixture was poured into ice water and the product was extracted with ethyl acetate. The extract was washed with water and dried and then the solvent was distilled off. The residue was purified by column chromatography on silica gel (isopropyl ether-ethyl acetate, 2:1) to obtain the desired compound (0.82 g, yield: 71.2%) as oil.

NMR (CDCl$_3$) δ1.21 (3H, t, J=7.2 Hz), 1.47 (3H, s), 1.98 (2H, m), 2.11 (3H, s), 2.14 (3H, s), 2.19 (3H, s), 2.70 (2H, m), 2.84 (2H, q, J=7.2 Hz), 2.85 (1H, broad s), 2.90 (1H, d, J=14.0 Hz), 3.02 (1H, d, J=14.0 Hz), 6.94 (2H, m), 7.12 (2H, m).

EXAMPLE 48

5-Methylamino-2,2,4,6,7-pentamethyl-2,3-dihydrobenzofuran hydrochloride

Lithium aluminum hydride (2.93 g, 77.2 mmol) was added with ice cooling to a solution of 5-amino-2,2,4,6,7-pentamethyl-2,3-dihydrofuran (9.00 g, 3.86 mmol) in tetrahydrofuran (150 ml). The mixture was heated under reflux for 5 hours. After the reaction mixture was cooled, water (4.8 ml) was added and the mixture was filtered. The filtrate was concentrated under reduced pressure and the residue was purified by column chromatography on silica gel (hexane-ethyl acetate, 9:1). The purified product was converted into its hydrochloride salt and the salt was recrystallized from ethanol-ether to obtain the desired compound (4.03 g, yield: 40.8%), m.p. 205°–208° C. (ethanol-ether).

NMR (CDCl$_3$) δ1.46 (6H, s), 2.08 (3H, s), 2.48 (6H, s), 2.92 (2H, s), 2.98–3.02 (3H, m), 10.57 (1H, broad s).

EXAMPLE 49

5-Ethylamino-2,2,4,6,7-pentamethyl-2,3-dihydrobenzofuran hydrochloride

The title compound was synthesized as oil according to the same manner as that described above (yield: 34.0%).

NMR (CDCl$_3$) δ1.45 (6H, s), 1.48 (3H, t, J=8.4 Hz), 2.07 (3H, s), 2.47 (3H, s), 2.48 (3H, s), 2.91 (2H, s), 3.35–3.48 (2H, m), 10.53 (1H, broad s).

EXAMPLE 50

2,2,4,6,7-Pentamethyl-5-propylamino-2,3-dihydrobenzofuran hydrochloride

The title compound was synthesized according to the same manner as that described above (yield: 43.2%), m.p. 185°–187° C. (ethanol-ether).

NMR (CDCl$_3$) δ0.92 (3H, t, J=7.4 Hz), 1.45 (6H, s), 1.93–2.06 (2H, m), 2.07 (3H, s), 2.47 (3H, s), 2.48 (3H, s), 2.91 (2H, s), 3.15–3.29 (2H, m), 10.54 (1H, broad s).

EXAMPLE 51

5-Butyrylamino-2,2,4,6,7-pentamethyl-2,3-dihydrobenzofuran hydrochloride

The title compound was synthesized according to the same manner as that described above (yield: 39.7%), m.p. 158°–160° C. (ethanol-ether).

NMR (CDCl$_3$) δ0.86 (3H, t, J=7.4 Hz), 1.23–1.38 (2H, m), 1.45 (6H, s), 1.91–2.06 (2H, m), 2.07 (3H, s), 2.47 (3H, s), 2.49 (2H, s), 3.17–3.32 (2H, m), 10.57 (1H. broad s).

EXAMPLE 52

5-Benzylamino-2,2,4,6,7-pentamethyl-2,3-dihydrobenzofuran hydrochloride

The title compound was synthesized according to the same manner as that described above (yield: 32.3%), m.p. 155°–157° C. (ethanol-ether).

NMR (CDCl$_3$) δ1.44 (6H, s), 2.02 (3H, s), 2.10 (3H, m), 2.20 (3H, s), 2.82 (2H, s), 4.56 (2H, broad s), 7.19–7.32 (5H, m), 10.89 (1H, broad s).

EXAMPLE 53

2,2,4,6,7-Pentamethyl-5-(2-methylpropyl)amino-2,3-dihydrobenzofuran hydrochloride The title compound was synthesized as oil according to the same manner as that described above (yield: 67.1%).

NMR (CDCl$_3$) δ1.10 (6H, d, J=6.6 Hz), 1.45 (6H, s), 2.05 (3H, s), 2.44 (3H, s), 2.48 (3H, s), 2.54–2.80 (1H, m), 2.90 (2H, s), 2.93–3.04 (2H, m), 10.39 (1H, broad s).

EXAMPLE 54

5-Acetylamino-4-dimethylamino-2,2,6,7-tetramethyl-2,3-dihydrobenzofuran

Potassium carbonate (4.42 g, 32.0 mmol) and methyl iodide (3.99 ml, 63.9 mmol) were added to a solution of 5-acetylamino-4-2,2,6,7-tetramethyl-2,3-dihydrobenzofuran (5.30 g, 21.3 mmol) in dimethylformamide (100 ml) and the mixture was stirred at room temperature for 3 hours. Water was added to the reaction mixture and the mixture was extracted with ethyl acetate. The extract was washed with water and dried and then the solvent was distilled off under reduced pressure. The residue was purified by column chromatography on silica gel (chloroform-methanol, 97:3) and recrystallized from dichloromethane-isopropyl ether to obtain the desired compound (5.52 g, yield: 93.6%), m.p. 186° C.

NMR (CDCl$_3$) δ1.44 (6H, s), 2.09 (6H, s), 2.21 (3H, s), 2.67 (6H, s), 3.09 (2H, s), 7.17 (1H, broad s).

EXAMPLE 55

5-Acetylamino-2,2,4,7-tetramethyl-6-dimethylamino-2,3-dihydrobenzofuran

The title compound was synthesized according to the same manner as that described above (yield: 93.5%), m.p. 142°–143° C. (isopropyl ether).

NMR (CDCl$_3$) δ1.46 (6H, s), 2.04 (3H, s), 2.10 (3H, s), 2.20 (3H, s), 2.78 (6H, s), 2.90 (2H, s), 7.05 (1H, broad s).

EXAMPLE 56

5-Amino-2,4,6,7-tetramethyl-2-dimethylaminomethyl-2,3-dihydrobenzofuran

Aqueous 50% dimethylamino solution (20 ml) was added to a solution of 2-bromomethyl-5-formylamino-2,4,6,7-tetramethyl-2,3-dihydrobenzofuran (4.0 g, 12.8 mmol) in methanol (20 ml) and heated at 160° C. for 15 hours in an autoclave. After the reaction mixture was cooled, the mixture was diluted with water and the product was extracted with ethyl acetate. The extract was washed with water and dried and then the solvent was distilled off. The residue was purified by column chromatography on silica gel (chloroform-methanol, 95:5) and then recrystallized from isopropyl ether to obtain the desired compound (2.9 g, yield: 91.2% yield), m.p. 66°–67° C.

NMR (CDCl$_3$) δ1.43 (3H, s), 2.07 (6H, s), 2.11 (3H, s), 2.33 (6H, s), 2.50 (2H, s), 2.82 (1H, d, J=15.4 Hz), 3.10 (2H, broad s), 3.12 (1H, d, J=15.4 Hz).

EXAMPLE 57

5-Amino-2,4,6,7-tetramethyl-2-pyrrolidinomethyl-2,3-dihydrobenzofuran

Pyrrolidine (20 ml) was added to 2-bromomethyl-5-formylamino-2,4,6,7-tetramethyl-2,3-dihydrobenzofuran (3.0 g, 9.6 mmol) and the mixture was heated at 160° C. in an autoclave for 15 hours. After the reaction mixture was cooled, the mixture was diluted with water and the product was extracted with ethylacetate. The extract was washed with water and dried and then the solvent was distilled off. The residue was purified by column chromatography on silica gel (chloroform-methanol, 9:1) and recrystallized from hexane to obtain the desired compound (2.2 g, yield: 83.5%), m.p. 85°–86° C. (dec.).

NMR (CDCl$_3$) δ1.44 ((3H, s), 1.72 (4H, m), 2.06 (6H, s), 2.10 (3H, s), 2.45–2.65 (4H, m), 2.68 (2H, s), 2.81 (1H, d, J=15,4 Hz), 3.16 (1H, d, J=15.4 Hz), 3.18 (2H, broad s).

EXAMPLE 58

5-Amino-2,4,6,7-tetramethyl-2-(4-methylpiperazino) methyl-2,3-dihydrobenzofuran

The title compound was synthesized according to the same manner as that described above (yield: 76.2%), m.p. 76°–77° C. (isopropyl ether).

NMR (CDCl$_3$) δ1.42 (3H, s), 2.07 (6H, s), 2.09 (3H, s), 2.25 (3H, s), 2.40 (4H, m), 2.48 (1H, d, J=14.2 Hz), 2.58 (1H, d, J=14.2 Hz), 2.50–2.80 (4H, m), 2.80 (1H, d, J=15.4 Hz), 3.11 (1H, d, J=15.4 Hz), 3.25 (2H, broad s).

EXAMPLE 59

5-Amino-2,4,6,7-tetramethyl-2-[N-(2-piperidinoethyl)aminomethyl]- 2,3-dihydrobenzofuran The title compound was synthesized according to the same manner as that described above (yield: 89.2%), m.p. 102°–104° C. (dichloromethane-isopropyl ether).

NMR (DMSO-d$_6$) δ1.44 (3H, s), 1.50–1.62 (6H, m), 1.73 (3H, broad s), 2.06 (3H, s), 2.08 (3H, s), 2.11 (3H, s), 2.36–2.48 (8H, m), 2.75–2.79 (3H, m), 3.13–3.22 (1H, m).

EXAMPLE 60

5-Amino-2,4,6,7-tetramethyl-2-(N-phenylaminomethyl)-2,3-dihydrobenzofuran hydrochloride The title compound was synthesized according to the same manner as that described above (yield: 35.5%), m.p. 162°–168° C. (ethanol-ether).

NMR (DMSO-d$_6$) δ1.45 (3H, s), 2.00 (3H, s), 2.20 (3H, s), 2.22 (3H, s), 2.90 (1H, d, J=16.4 Hz), 3.22 (1H, d, J=16.4 Hz), 3.31 (2H, s), 6.61 (1H, t, J=7.8 Hz), 6.74 (2H, d, J=7.8 Hz), 7.08 (2H, t, J=7.8 Hz), 9.78 (3H, broad s).

EXAMPLE 61

5-Amino-2-(N-benzylaminomethyl)-2,4,6,7-tetramethyl-2,3-dihydrobenzofuran dihydrochloride The title compound was synthesized according to the same manner as that described above (yield: 64.7%), m.p. 228°–232° C. (ethanol-ether).

NMR (DMSO-d$_6$) δ1.48 (3H, s), 2.07 (3H, s), 2.22 (3H, s), 2.23 (3H, s), 2.93 (1H, d, J=16.2 Hz), 3.10 (2H, s), 3.41 (1H, d, J=16.2 Hz), 4.19 (2H, s), 7.38–7.42 (3H, m), 7.60–7.65 (2H, m), 9.70 (3H, broad s).

EXAMPLE 62

5-Amino-2,4,6,7-tetramethyl-2-(N-phenethylaminomethyl)-2,3-dihydrobenzofuran dihydrochloride The title compound was synthesized according to the same manner as that described above (yield: 63.1%), m.p. 178°–181° C. (ethanol).

NMR (DMSO-d$_6$) δ1.52 (3H, s), 2.08 (3H, s), 2.23 (3H, s), 2.24 (3h, s), 2.95–3.50 (8H, s), 7.22–7.38 (5H, m), 9.19 and 9.72 (3H, broad s).

EXAMPLE 63

5-Amino-2,4,6,7-tetramethyl-2-[N-(4-phenylbutyl) aminomethyl]-2,3-dihydrobenzofuran dihydrochloride The title compound was synthesized according to the same manner as that described above (yield: 72.6%), m.p. 201°–202° C. (ethanol-ether).

NMR (DMSO-d$_6$) δ1.50 (3H, s), 1.53–1.74 (4H, m), 2.07 (3H, s), 2.24 (6H, s), 2.59 (2H, t, J=7.0 Hz), 2.91–3.00 (3H, m), 3.22 (2H, s), 3.43 (1H, d, J=15.8 Hz), 7.16–7.29 (5H, m), 9.08 and 9.88 (3H, broad s).

EXAMPLE 64

5-Amino-2,4,6,7-tetramethyl-2-[N-(3-pyridylmethyl) aminomethyl]-2,3-dihydrobenzofuran trihydrochloride The title compound was synthesized according to the same manner as that described above (yield: 54.6%), m.p. 208°–213° C. (ethanol-ether).

NMR (DMSO-d$_6$) δ1.51 (3H, s), 2.09 (3H, s), 2.23 (6H, s), 2.95 (1H, d, J=16.0 Hz), 3.28 (2H, s), 3.50 (1H, d, J=16.0 Hz), 4.43 (2H, s), 7.97 (1H, dd, J=5.4 Hz, 8.0 Hz), 8.74 (1H, d, J=8.0 Hz), 8.88 (1H, d, J=5.4 Hz), 9.13 (1H, s), 9.93 (3H, broad s).

EXAMPLE 65

5-Amino-2-(1-imidazolyl)methyl-2,4,6,7-tetramethyl-2,3-dihydrobenzofuran dihydrochloride Imidazole (10.0 g, 147 mmol) was added to a suspension of 2-bromomethyl-5-formylamino-2,4,6,7-tetramethyl-2,3-dihydrobenzofuran (3.12 g, 10 mmol) in toluene (30 ml) and the mixture was heated at 200° C. in an autoclave for 15 hours. The reaction mixture was washed with water, dried and the solvent was distilled off. The residue was dissolved in methanol (30 ml). Aqueous 6N sodium hydroxide solution was added to the mixture and the resulting mixture was heated under reflux for 1 hour. The mixture was diluted with water and the product was extracted with ethyl acetate. The extract was washed with water, dried and the solvent was distilled off. The residue was purified by column chromatography on silica gel (chloroform-methanol, 95:5). The purified product was converted into its hydrochloride salt and then recrystallized from ethanol-isopropyl ether to obtain the desired compound (1.3 g, yield: 37.8% yield), m.p. 278°–283° C. (dec.).

NMR (DMSO-d$_6$) δ1.41 (3H, s), 2.08 (3H, s), 2.24 (6H, s), 3.09 (1H, d, J=16.2 Hz), 3.23 (1H, d, J=16.2 Hz), 4.54 (2H, s), 7.66 (1H, d, J=1.6 Hz), 7.73 (1H, d, J=1.6 Hz), 9.19 (1H, s), 10.8 (2H, broad s).

EXAMPLE 66

5-Amino-2,4,6,7-tetramethyl-2-(4-phenylpiperazino) methyl-2,3-dihydrobenzofuran

The title compound was synthesized according to the same manner as that described above (yield: 18.3%), m.p. 94°–950° C. (isopropyl ether).

NMR (CDCl$_3$) δ1.45 (3H, s), 2.08 (6H, s), 2.12 (3H, s), 2.55–2.90 (8H, m), 2.90–3.50 (6H, m), 6.80–7.00 (3H, m), 7.25 (2H, m).

EXAMPLE 67

5-Amino-2,4,6,7-tetramethyl-2-(4-phenylpiperidino) methyl-2,3-dihydrobenzofuran

The title compound was synthesized according to the same manner as that described above (yield: 57.55), m.p. 112°–113° C. (isopropyl ether).

NMR (CDCl$_3$) δ1.47 (3H, s), 1.75 (4H, m), 2.09 (6H, s), 2.13 (3H, s), 2.15–2.50 (4H, m), 2.54 (1H, d, J=14.0 Hz), 2.63 (1H, d, J=14.0 Hz) 2.84 (1H, d, J=15.2 Hz), 2.99 (1H, m), 3.15 (1H, d, J=15.2 Hz), 3.19 (2H, broad s), 7.27 (5H, m).

EXAMPLE 68

5-Amino-2,4,6,7-tetramethyl-2-[4-(diphenylmethyl) piperazinomethyl]-2,3-dihydrobenzofuran dihydrochloride The title compound was synthesized according to the same manner as that described above (yield: 17.7%), m.p. 193°–196° C. (dec.) (ethanol-ether).

NMR (DMSO-d$_6$) δ1.50 (3H, s), 1.99 (6H, s), 2.21 (3H, s), 3.03–3.51 (12H, m), 5.20 (1H, broad s), 7.33–7.45 (6H, m), 7.68 (4H, broad s).

EXAMPLE 69

5-Amino-2-benzyloxymethyl-2,4,6,7-tetramethyl-2, 3-dihydrobenzofuran hydrochloride Benzylalcohol (20 ml) and sodium hydride (60% purity, 1.0 g, 25 mmol) were added to 2-bromomethyl-5-formylamino-2,4,6,7-tetramethyl-2,3-dihydrobenzofuran (2.0 g, 6.4 mmol) and the mixture was heated at 180° C. in an autoclave for 18 hours. After the reaction mixture was cooled, the mixture was diluted with water and the product was extracted with ethyl acetate. The extract was washed with water and dried and then the solvent was distilled off. The residue was purified by column chromatography on silica gel (isopropyl ether). The purified product was converted into its hydrochloride salt and then recrystallized from ethanol-isopropyl ether to obtain the desired compound (0.68 g, yield: 30.5%), m.p. 195°–200° C.

NMR (DMSO-d$_6$) δ1.40 (3H, s), 2.05 (3H, s), 2.22 (6H, s), 2.88 (1H, d, J=15.8 Hz), 3.17 (1H, d, J=15.8 Hz), 3.51 (2H, s), 4.56 (2H, s), 7.31 (5H, m), 9.71 (2H, broad s).

EXAMPLE 70

5-Amino-2-methoxy-2,4,6,7-tetramethyl-2,3-dihydrobenzofuran hydrochloride

The title compound was synthesized according to the same manner as that described above (yield: 49.6%), m.p. 180°–182° C (ethanol-isopropyl ether).

NMR (DMSO-d$_6$) δ1.37 (3H, s), 2.04 (3H, s), 2.22 (6H, s), 2.85 (1H, d, J=16.0 Hz), 3.14 (1H, d, J=16.0 Hz), 3.31 (3H, s), 3.43 (2H, s), 9.77 (2H, broad s).

EXAMPLE 71

5-Amino-2,4,6,7-tetramethyl-2-[2-(dimethylamino) ethoxymethyl]-2,3-dihydrobenzofuran The title compound was synthesized as an amorphous product according to the same manner as that described above (yield: 67.8%).

NMR (DMSO-d$_6$) δ1.40 (3H, s), 2.02 (3H, s), 2.21 (3H, s), 2.23 (3H, s), 2.69 (2H, broad s), 2.81–3.44 (12H, m), 9.79 (2H, broad s).

EXAMPLE 72

5-Formylamino-2,4,6,7-tetramethyl-2-phenylthiomethyl-2,3-dihydrobenzofuran

Sodium hydride (60% purity, 1.0 g, 21.1 mmol) was added to a solution of 2-bromomethyl-5-formylamino-2,4,6,7-tetramethyl-2,3-dihydrobenzofuran (6.0 g, 19.2 mmol) and thiophenol in dimethylformamide (50 ml) and the mixture was stirred at 80° C. for 1 hour under an argon atmosphere. After the reaction mixture was cooled, the product was extracted with ethyl acetate. The extract was washed with water, dried and the solvent was distilled off. The residue was purified by column chromatography on silica gel (isopropyl ether-ethyl acetate, 1:1) and then the purified product was recrystallized from ethanol-isopropyl ether to obtain the desired compound (5.54 g, yield: 83.3% yield), m.p. 130°14 131° C.

NMR (CDCl$_3$) δ1.55 (1.5H, s), 1.56 (1.5H, s), 2.00 (3H, s), 2.06 (1.5H, s), 2.09 (1.5H, s), 2.11 (1.5H, s), 2.14 (1.5H, s), 2.91 (1H, d, J=15.8 Hz), 3.23 (0.5H, d, J=15.8 Hz), 3.43 (0.5H, d, J=15.8 Hz), 3.27 (2H, s), 6.74 (0.5H, broad s), 6.84 (0.5H, d, J=12.0 Hz), 7.15–7.40 (5H, m), 7.97 (0.5H, d, J=12.0 Hz), 8.40 (0.5H, 1.4 Hz).

EXAMPLE 73

2-(4-Fluorophenyl) thiomethyl-5-formylamino-2,4, 6,7-tetramethyl-2,3-dihydrobenzofuran The title compound was synthesized as oil according to the same manner as that described above (yield: 95.6%).

NMR (CDCl$_3$) δ1.53 (1.5H, s), 1.55 (1.5H, s), 2.05 (3H, s), 2.06 (1.5H, s), 2.11 (3H, s), 2.14 (1.5H, s), 2.91 (1H, d, J=15.8 Hz), 3.21 (2H, s), 3.22 (0.5H, d, J=15.8 Hz), 3.25 (0.5H, d, J=15.8 Hz), 6.74 (0.5H, broad s), 6.82 (0.5H, d, J=12.2 Hz), 6.95 (2H, t, J=9.0 Hz), 7.36 (2H, dd, J=5.2 Hz and 9.0 Hz), 7.97 (0.5H, d, J=12.2 Hz), 8.40 (0.5H, d, J=1.6 Hz).

EXAMPLE 74

5-Formylamino-2-(4-hydroxyphenyl)thiomethyl-2,4, 6,7-tetramethyl-2,3-dihydrobenzofuran The title compound was synthesized as oil according to the same manner as that described above (yield: 93.1%).

NMR (CDCl$_3$) δ1.51 (1.5H, s), 1.53 (1.5H, s), 1.99 (1.5H, s), 2.01 (1.5H, s), 2.03 (1.5H, s), 2.07 (1.5H, s), 2.10 (1.5H, s), 2.14 (1.5H, s), 2.84 (0.5H, d, J=15.4 Hz), 2.87 (0.5H, d, J=15.8 Hz), 3.10 (0.5H, d, J=15.4 Hz), 3.11 (0.5H, d, J=15.8 Hz), 3.20 (0.5H, d, J=15.8 Hz), 3.21 (0.5H, d, J=15.8 Hz), 3.22 (0.5H, d, J=15.4 Hz), 3.23 (0.5H, d, J=15.8 Hz), 6.01 (0.5H, broad s), 6.15 (0.5H, broad s), 6.70 (2H, m), 6.81 (0.5H, broad s), 6.85 (1.5H, broad s), 7.25 (2H, m), 7.95 (0.5H, d, J=11.8 Hz), 8.39 (0.5H, d, J=1.6 Hz).

EXAMPLE 75

5-Formylamino-2,4,6,7-tetramethyl-2-(1-methyl-2-imidazolyl) thiomethyl-2,3-dihydrobenzofuran The title compound was synthesized as oil according to the same manner as that described above (yield: 88.6%).

NMR (CDCl$_3$) δ1.53 (1.5H, s), 1.55 (1.5H, s), 1.97 (1.5H, s), 2.03 (1.5H, s), 2.04 (1.5H, s), 2.10 (3H, s), 2.14 (1.5H, s), 2.89 (1H, d, J=15.6 Hz), 3.18 (0.5H, d, J=15.6 Hz), 3.24 (0.5H, d, J=15.6 Hz), 3.47 (2H, s), 3.49 (1.5H, s), 3.52 (1.5H, s), 6.87 (1H, m), 6.99 (0.5H, d, J=12.0 Hz), 7.00 (1H, m), 7.11 (0.5H, broad s), 7.95 (0.5H, d, J=12.0 Hz), 8.37 (0.5H, d, J=1.4 Hz).

EXAMPLE 76

2-(2-Benzothiazolyl)thiomethyl-5-formylamino-2,4,6,7-tetramethyl-2,3-dihydrobenzofuran The title compound was synthesized according to the same manner as that described above (yield: 88.2%), m.p. 190°–192° C. (isopropyl ether).

NMR (CDCl$_3$) δ1.64 (3H, s), 2.00 (3H, s), 2.07 (1.5H, s), 2.10 (1.5H, s), 2.11 (1.5H, s), 2.14 (1.5H, s), 2.99 (1H, d, J=15.8 Hz), 3.27 (0.5H, d, J=15.8 Hz), 3.29 (0.5H, d, J=15.8 Hz), 3.78 (0.5H, d, J=15.4 Hz), 3.79 (0.5H, d, J=15.4 Hz), 3.87 (0.5H, d, J=15.4 Hz), 3.88 (0.5H, d, J=15.4 Hz), 6.73 (0.5H, broad s), 6.75 (0.5H, d, J=12.0 Hz), 7.20–7.50 (2H, m), 7.70–7.85 (2H, m), 7.97 (0.5H, d, J=12.0 Hz), 8.40 (0.5H, d, J=1.6 Hz).

EXAMPLE 77

5-Formylamino-2,4,6,7-tetramethyl-2-(4-pyridyl)thiomethyl-2,3-dihydrobenzofuran

The title compound was synthesized as oil according to the same manner as that described above (yield: 71.6%).

NMR (CDCl$_3$) δ1.59 (1.5H, s), 1.61 (1.5H, s), 1.97 (3H, s), 2.08 (1.5H, s), 2.10 (1.5H, s), 2.13 (1.5H, s), 2.14 (1.5H, s), 2.98 (1H, d, J=16.0 Hz), 3.25 (0.5H, d, J=16.0 Hz), 3.30 (0.5H, d, J=16.0 Hz), 3.31 (2H, s), 7.00 (0.5H, d, J=12.0 Hz), 7.05 (0.5H, broad s), 7.17 (2H, dd, J=1.6 Hz and 6.2 Hz), 7.98 (0.5H, d, J=12.0 Hz), 8.36 (2H, dd, J=1.6 Hz and 6.2 Hz), 8.37 (0.5H, d, J=1.6 Hz).

EXAMPLE 78

2-Benzylthiomethyl-5-formylamino-2,4,6,7-tetramethyl-2,3-dihydrobenzofuran

The title compound was synthesized as oil according to the same manner as that described above (yield: 83.5%).

NMR (CDCl$_3$) δ1.49 (1.5H, s), 1.50 (1.5H, s), 2.08 (1.5H, s), 2.12 (6H, s), 2.16 (1.5H, s), 2.71 (1H, d, J=13.4 Hz), 2.77 (1H, d, J=13.4 Hz), 2.86 (1H, d, J=15.0 Hz), 3.18 (1H, d, J=15.0 Hz), 3.74 (1H, d, J=13.2 Hz), 3.18 (1H, d, J=13.2 Hz), 6.76 (0.5H, broad s), 6.87 (0.5H, d, J=12.0 Hz), 7.30 (5H, m), 7.98 (0.5H, d, J=12.0 Hz), 8.40 (0.5H, d, J=1.4 Hz).

EXAMPLE 79

5-Formylamino-2,4,6,7-tetramethyl-2-propylthiomethyl-2,3-dihydrobenzofuran

The title compound was synthesized as oil according to the same manner as that described above (yield: 93.0%).

NMR (CDCl$_3$) δ0.96 (3H, t, J=7.4 Hz), 1.52 (1.5H, s), 1.54 (1.5H, s), 1.60 (2H, m), 2.08 (3H, s), 2.10 (1.5H, s), 2.12 (1.5H, s), 2.13 (1.5H, s), 2.16 (1.5H, s), 2.58 (2H, dt, J=7.2 Hz and 1.2 Hz), 2.82 (1H, s), 2.84 (1H, s), 2.89 (1H, d, J=15.8 Hz), 3.22 (0.5H, d, J=15.8 Hz), 3.24 (0.5H, d, J=15.8 Hz), 6.77 (0.5H, broad s), 6.85 (0.5H, d, J=12.0 Hz), 7.97 (0.5H, d, J=12.0 Hz), 8.40 (0.5H, d, J=1.6 Hz).

EXAMPLE 80

5-Formylamino-2-(2-hydroxyethyl)thiomethyl-2,4,6,7-tetramethyl-2,3-dihydrobenzofuran The title compound was synthesized as oil according to the same manner as that described above (yield: 57.2%).

NMR (CDCl$_3$) δ1.52 (1.5H, s), 1.54 (1.5H, s), 2.09 (3H, s), 2.11 (1.5H, s), 2.12 (1.5H, s), 2.13 (1.5H, s), 2.16 (1.5H, s), 2.29 (0.5H, t, J=6.4 Hz), 2.35 (0.5H, t, J=6.4 Hz), 2.80 (2H, dt, J=7.2 Hz and 1.2 Hz), 2.87 (0.5H, s), 2.89 (1H, s), 2.91 (1H, d, J=15.4 Hz), 3.20 (0.5H, d, J=15.4 Hz), 3.22 (0.5H, d, J=15.4 Hz), 3.73 (2H, m), 6.78 (0.5H, broad s), 6.80 (0.5H, d, J=12.0 Hz), 7.97 (0.5H, d, J=12.0 Hz), 8.38 (0.5H, d, J=1.4 Hz).

EXAMPLE 81

3-[(5-Formylamino-2,4,6,7-tetramethyl-2,3-dihydrobenzofuran-2-yl) methylthio] propionic acid The title compound was synthesized as oil according to the same manner as that described above (yield: 94.7%).

NMR (CDCl$_3$) δ1.52 (1.5H, s), 1.54 (1.5H, s), 2.08 (3H, s), 2.09 (3H, s), 2.12 (1.5H, s), 2.14 (1.5H, s), 2.64 (2H, t, J=7.0 Hz), 2.86 (2H, t, J=7.0 Hz), 2.87 (2H, s), 2.90 (1H, d, J=15.4 Hz), 3.22 (1H, d, J=15.4 Hz), 6.50 (0.5H, broad s), 6.95 (0.5H, broad s), 7.96 (0.5H, broad s), 8.38 (0.5H, d, J=1.6 Hz).

EXAMPLE 82

5-Formylamino-2,4,6,7-tetramethyl-2,3-dihydrobenzofuran- 2-yl phenylsulfoxide

5-Formylamino-2,4,6,7-tetramethyl-2-phenylthiomethyl-2,3-dihydrobenzofuran (2.3 g, 6.7 mmol) was dissolved in methanol (20 ml). Aqueous 1M sodium metaperiodate solution (20 ml) was added to the solution and the mixture was stirred for 3 hours. The reaction mixture was diluted with water and the product was extracted with ethyl acetate. The extract was washed with water, dried and the solvent was distilled off. The residue was crystallized from isopropyl ether-ethyl acetate to obtain the desired compound (1.54 g, yield: 64.0% yield), m.p. 112°–115° C. (dec.).

NMR (CDCl$_3$) δ1.62 (3H, s), 2.08 (3H, s), 2.12 (1.5H, s), 2.14 (1.5H, s), 2.16 (1.5H, s), 2.18 (1.5H, s), 3.00–3.40 (4H, m), 6.78 (1H, m), 7.45–7.70 (5H, m), 7.96 (0.25H, d, J=12.0 Hz), 7.99 (0.25H, d, J=12.0 Hz), 8.40 (0.25H, d, J=1.4 Hz), 8.42 (0.25H, d, J=1.4 Hz).

EXAMPLE 83

5-Formylamino-2,4,6,7-tetramethyl-2,3-dihydrobenzofuran-2-yl phenylsulfone

5-Formylamino-2,4,6,7-tetramethyl-2-phenylthiomethyl-2,3-dihydrobenzofuran (2.1 g, 6.2 mmol) was dissolved in methanol (20 ml). Aqueous 2M sodium metaperiodate solution (20 ml) was added to the solution and the mixture was heated under reflux for 3 hours. The reaction mixture was diluted with water and the product was extracted with ethyl acetate. The extract was washed with water, dried and the solvent was distilled off. The residue was crystallized from isopropyl ether-ethyl acetate to obtain the desired compound (1.40 g, yield: 65.9% yield), m.p. 154°–155° C.

NMR (CDCl$_3$) δ1.70 (1.5H, s), 1.71 (1.5H, s), 1.81 (1.5H, s), 1.84 (1.5H, s), 2.05 (1.5H, s), 2.07 (1.5H, s), 2.12 (1.5H, s), 2.14 (1.5H, s), 3.01 (1H, d, J=15.6 Hz), 3.56 (1H, s), 3.58 (1H, s), 3.62 (0.5H, d, J=15.6 Hz), 3.67 (0.5H, d, J=15.6 Hz), 6.71 (0.5H, broad s), 6.74 (0.5H, d, J=12.0 Hz), 7.15–7.70 (3H, m), 7.89 (2H, m), 7.96 (0.5H, d, J=12.0 Hz), 8.40 (0.5H, d, J=1.6 Hz).

EXAMPLE 84

5-Amino-2,4,6,7-tetramethyl-2-(2-phenylethyl)-2,3-dihydrobenzofuran

Aqueous 6N sodium hydroxide solution (3 ml) was added to a solution of 5-acetylamino-2,4,6,7-tetramethyl-2-(2- phenylethyl)-2,3-dihydrobenzofuran (0.7 g, 2.1 mmol) in methanol (3 ml) and the mixture was heated at 200° C. in an autoclave for 18 hours. The reaction mixture was diluted with water and the product was extracted with ethyl acetate. The extract was washed with water, dried and concentrated. The residue was purified by column chromatography on silica gel (isopropyl ether-ethyl acetate, 2:1). The crude crystals were recrystallized from hexane to obtain the desired compound (0.32 g, yield: 54.5%), m.p. 45°– 46° C.(dec.).

NMR (CDCl$_3$) δ1.47 (3H, s), 2.03 (2H, m), 2.07 (3H, s), 2.09 (3H, s), 2.14 (3H, s), 2.76 (2H, m), 2.92 (1H, d, J=15.4 Hz), 3.00 (2H, broad s), 3.07 (1H, d, J=15.4 Hz), 7.10–7.30 (5H, m).

EXAMPLE 85

5-Amino-2,4,6,7-tetramethyl-2-[2-(4-fluorophenyl) ethyl]-2,3-dihydrobenzofuran

The title compound was synthesized according to the same manner as that described above (yield: 54.6%), m.p. 62°–63° C. (hexane).

NMR (CDCl$_3$) δ1.47 (3H, s), 1.98 (2H, m), 2.10 (3H, s), 2.14 (3H, s), 2.19 (3H, s), 2.72 (2H, m), 2.90 (1H, d, J=14.0 Hz), 3.00 (2H, broad s), 3.05 (1H, d, J=14.0 Hz), 6.95 (2H, m), 7.13 (2H, m).

EXAMPLE 86

Methyl 3-[5-amino-2,4,6,7-tetramethyl-2,3-dihydrobenzofuran-2-yl] acrylate hydrochloride 3-[5-Acetylamino-2,4,6,7-tetramethyl-2,3-dihydrobenzofuran-2-yl] acrylic acid ethyl ester (0.5 g, 1.58 mmol) was dissolved in methanol (5 ml). Conc. hydrochloric acid (5 ml) was added to the solution and the mixture was heated under reflux for 1 hour. The reaction mixture was cooled and the crystals precipitated were filtered. The crude crystals obtained were recrystallized from ethanol-isopropyl ether to obtain the desired compound (0.35 g, yield: 74.7% yield), m.p. 225°–234° C. (dec.).

NMR (DMSO-d$_6$) δ1.58 (3H, s), 2.11 (3H, s), 2.19 (3H, s), 2.21 (3H, s), 3.12 (1H, d, J=15.0 Hz), 3.24 (1H, d, J=15.0 Hz), 3.65 (3H, s), 5.93 (1H, d, J=16.0 Hz), 7.04 (1H, d, J=16.0 Hz), 9.50 (2H, broad s).

EXAMPLE 87

5-Amino-2-bromomethyl-2,4,6,7-tetramethyl-2,3-dihydrobenzofuran hydrochloride

The title compound was synthesized according to the same manner as that described above (yield: 90.2%), m.p. 235°–245° C. (ethanol-isopropyl ether).

NMR (DMSO-d$_6$) δ1.53 (3H, s), 2.04 (3H, s) 2.23 (3H, s), 2.24 (3H, s), 3.03 (1H, d, J=16.0 Hz), 3.27 (1H, d, J=16.0 Hz), 3.77 (2H, s), 9.85 (2H, broad s).

EXAMPLE 88

5-Amino-2-phenylthiomethyl-2,4,6,7-tetramethyl-2, 3-dihydrobenzofuran hydrochloride The title compound was synthesized according to the same manner as that described above (yield: 94.5%), m.p. 130°–131° C. (ethanol-isopropyl ether).

NMR (DMSO-d$_6$) δ1.51 (3H, s), 1.87 (3H, s), 2.19 (3H, s), 2.20 (3H, s), 2.99 (1H, d, J=15.8 Hz), 3.22 (1H, d, J=15.8 Hz), 3.38 (2H, s), 7.10–7.40 (5H, m), 9.69 (2H, broad s).

EXAMPLE 89

5-Amino-2-(4-fluorophenyl)thiomethyl-2,4,6,7-tetramethyl- 2,3-dihydrobenzofuran hydrochloride The title compound was synthesized according to the same manner as that described above, (yield: 80.9%), m.p. 204°–210° C. (dec.) (ethanol-isopropyl ether).

NMR (DMSO-d$_6$) δ1.49 (3H, s), 1.84 (3H, s), 2.19 (3H, s), 2.20 (3H, s), 2.98 (1H, d, J=15.8 Hz), 3.21 (1H, d, J=15.8 Hz), 3.31 (1H, d, J=14.0 Hz), 3.39 (1H, d, J=14.0 Hz), 7.13 (2H, t, J=9.0 Hz), 7.38 (2H, dd, J=9.0 Hz and 5.4 Hz), 9.67 (2H, broad s).

EXAMPLE 90

5-Amino-2-(4-hydroxyphenyl)thiomethyl-2,4,6,7-tetramethyl-2,3-dihydrobenzofuran hydrochloride The title compound was synthesized according to the same manner as that described above (yield: 96.2%), m.p. 230°–236° C. (dec.) (ethanol-isopropyl ether).

NMR (DMSO-d$_6$) δ1.46 (3H, s), 1.91 (3H, s), 2.18 (6H, s), 2.94 (1H, d, J=15.8 Hz), 3.20 (1H, d, J=15.8 Hz), 3.20 (2H, s), 6.70 (2H, d, J=8.6 Hz), 7.19 (2H, d, J=8.6 Hz), 9.45 (2H, broad s), 9.56 (1H, s).

EXAMPLE 91

5-Amino-2-(1-methylimidazol-2-yl)thiomethyl-2,4, 6,7-tetramethyl-2,3-dihydrobenzofuran dihydrochloride The title compound was synthesized according to the same manner as that described above (yield: 65.3% yield), m.p. 220°–225° C. (dec.) (ethanol-isopropyl ether).

NMR (DMSO-d$_6$) δ1.50 (3H, s), 1.72 (3H, s), 2.19 (3H, s), 2.24 (3H, s), 3.05 (1H, d, J=16.2 Hz), 3.29 (1H, d, J=16.2 Hz), 3.50 (3H, s), 3.56 (1H, d, J=14.6 Hz), 3.84 (1H, d, J=14.6 Hz), 7.71 (1H, d, J=1.8 Hz), 7.75 (1H, d, J=1.8 Hz), 10.2 (2H, broad s).

EXAMPLE 92

5-Amino-2-(2-benzothiazolyl)thiomethyl-2,4,6,7-tetramethyl-2,3-dihydrobenzofuran hydrochloride The title compound was synthesized according to the same manner as that described above (yield: 89.1%), m.p. 204°–208° C. (dec.) (ethanol-isopropyl ether).

NMR (DMSO-d$_6$) δ1.58 (3H, s), 1.76 (3H, s), 2.16 (3H, s), 2.21 (3H, s), 3.08 (1H, d, J=15.8 Hz), 3.28 (1H, d, J=15.8 Hz), 3.79 (1H, d, J=14.6 Hz), 3.88 (1H, d, J=14.6 Hz), 7.37 (1H, t, J=7.6 Hz), 7.47 (1H, t, J=7.6 Hz), 7.78 (1H, d, J=7.6 Hz), 8.01 (1H, d, J=7.6 Hz), 9.65 (2H, broad s).

EXAMPLE 93

5-Amino-2-benzylthiomethyl-2,4,6,7-tetramethyl-2, 3-dihydrobenzofuran hydrochloride The title compound was synthesized according to the same manner as that described above (yield: 74.1%), m.p. 170°–172° C. (ethanol-isopropyl ether).

NMR (DMSO-d$_6$) δ1.44 (3H, s), 2.07 (3H, s), 2.23 (6H, s), 2.80 (2H, s), 2.93 (1H, d, J=16.0 Hz), 3.13 (1H, d, J=16.0 Hz), 3.77 (1H, d, J=13.8 Hz), 3.87 (1H, d, J=13.8 Hz), 7.29 (5H, m), 9.77 (2H, broad s).

EXAMPLE 94

5-Amino-2,4,6,7-tetramethyl-2-(4-pyridyl) thiomethyl-2,3-dihydrobenzofuran

The title compound was synthesized according to the same manner as that described above (yield: 80.4%), m.p. 96°–97° C. (ethyl acetate-isopropyl ether).

NMR (CDCl$_3$) δ1.58 (3H, s), 2.00 (3H, s), 2.05 (3H, s), 2.06 (3H, s), 2.85 (2H, broad s), 2.98 (1H, d, J=15.6 Hz), 3.21 (1H, d, J=15.6 Hz), 3.25 (1H, d, J=14.0 Hz), 3.32 (1H, d, J=14.0 Hz), 7.14 (2H, dd, J=4.8 Hz and 2.0 Hz), 8.33 (2H, dd, J=4.8 Hz and 2.0 Hz).

EXAMPLE 95

5-Amino-2,4,6,7-tetramethyl-2-propylthiomethyl-2,3-dihydrobenzofuran hydrochloride The title compound was synthesized according to the same manner as that described above (yield: 74.6%), m.p. 186°–188° C. (ethanol-isopropyl ether).

NMR (DMSO-d$_6$) δ0.97 (3H, t, J=7.4 Hz), 1.40–1.70 (2H, m), 1.53 (3H, s), 2.09 (3H, s), 2.50 (6H, s), 2.45–2.60 (2H, m), 2.82 (2H, s), 2.88 (1H, d, J=15.4 Hz), 3.28 (1H, d, J=15.4 Hz), 10.10 (2H, broad s).

EXAMPLE 96

5-Amino-2-(2-hydroxyethyl)thiomethyl-2,4,6,7-tetramethyl-2,3-dihydrobenzofuran

The title compound was synthesized according to the same manner as that described above (yield: 32.3%), m.p. 108°–109° C. (ethyl acetate-isopropyl ether).

NMR (CDCl$_3$) δ1.51 (3H, s), 2.07 (3H, s), 2.08 (3H, s), 2.11 (3H, s), 2.80 (1H, broad s), 2.81 (2H, t, J=5.4 Hz), 2.82(1H, d, J=15.0 Hz), 2.90 (1H, d, J=15.0 Hz), 2.92 (1H, d, J=15.4 Hz), 3.19 (1H, d, J=15.4 Hz), 3.20 (2H, broad s), 3.73 (2H, t, J=5.4 Hz).

EXAMPLE 97

3-[(5-Amino-2,4,6,7-tetramethyl-2,3-dihydrobenzofuran-2-yl) methylthio] propionic acid The title compound was synthesized according to the same manner as that described above (yield: 77.5%), m.p. 139°–140° C. (ethyl acetate-isopropyl ether).

NMR (CDCl$_3$) δ1.51 (3H, s), 2.07 (6H, s), 2.09 (3H, s), 2.64 (2H, t, J=6.8 Hz), 2.80 (1H, d, J=14.0 Hz), 2.87 (1H, d, J=14.0 Hz), 2.88 (2H, t, J=6.8 Hz), 2.91 (1H, d, J=15.4 Hz), 3.20 (1H, d, J=15.4 Hz), 4.90 (3H, broad s).

EXAMPLE 98

5-Amino-2,4,6,7-tetramethyl-2,3-dihydrobenzofuran-2-yl phenylsulfoxide

The title compound was synthesized as oil according to the same manner as that described above (yield: 21.0%).

NMR (CDCl$_3$) δ1.60 (1.5H, s), 1.84 (1.5H, s), 2.04 (1.5H, s), 2.09 (4.5H, s), 2.11 (3H, s), 2.90–3.45 (5.5H, m), 3.69 (0.5H, d, J=15.8 Hz), 7.48 (3H, m), 7.63 (2H, m).

EXAMPLE 99

5-Amino-2,4,6,7-tetramethyl-2,3-dihydrobenzofuran-2-yl phenylsulfone

The title compound was synthesized according to the same manner as that described above (yield: 91.7% yield), m.p. 150°–151° C. (ethyl acetate-isopropyl ether).

NMR (CDCl$_3$) δ1.69 (3H, s), 1.81 (3H, s), 2.02 (3H, s), 2.05 (3H, s), 2.99 (1H, d, J=15.6 Hz), 3.30 (2H, broad s), 3.54 (2H, s), 3.60 (1H, d, J=15.6 Hz), 7.40–7.70 (3H, m), 7.85 (2H, m).

EXAMPLE 100

5-Amino-2,2,6,7-tetramethyl-4-nitro-2,3-dihydrobenzofuran hydrochloride

The title compound was synthesized according to the same manner as that described above (yield: 79.6%), m.p. 119°–121° C. (ethanol-ether).

NMR (CDCl$_3$) δ1.48 (6H, s), 2.20 (3H, s), 2.54 (3H, s), 3.42 (2H, s), 8.61 (2H, broad s).

EXAMPLE 101

5-Amino-2,2,6,7-tetramethyl-4-dimethylamino-2,3-dihydrobenzofuran dihydrochloride The title compound was synthesized according to the same manner as that described above (yield: 64.5%), m.p. 240°–244° C. (ethanol).

NMR (DMSO-d$_6$) δ1.42 (6H, s), 2.02 (3H, s), 2.18 (3H, s), 2.63 (6H, s), 3.17 (2H, s), 4.94 (2H, broad s).

EXAMPLE 102

5-Amino-2,2,4,7-tetramethyl-6-dimethylamino-2,3-dihydrobenzofuran hydrochloride

The title compound was synthesized according to the same manner as that described above (yield: 63.2%), m.p. 236°–238° C. (ethanol).

NMR (DMSO-d6) δ1.41 (6H, s), 2.10 (3H, s), 2.19 (3H, s), 2.72 (6H, s), 2.96 (2H, s), 9.66 (2H, broad s).

EXAMPLE 103

5-Amino-2,2,4,6,7-pentamethyl-2,3-dihydrobenzofuran

Sulfuric acid (2.0 ml) was added to a solution of 4-amino-2,3,5-trimethylphenol (2.0 g, 13.2 mmol) and 2-methyl-2-propenol (1.15 g, 15.8 mmol) in dichloromethane (20 ml) and the mixture was heated under reflux for 18 hours under an argon atmosphere. The reaction solution was made weak alkaline with aqueous saturated sodium bicarbonate solution and the organic layer was separated. The organic layer was washed with water, dried and then concentrated. The residue was purified by column chromatography on silica gel eluting with isopropyl ether. The product obtained was recrystallized from hexane to obtain the desired product as crystals (460 mg, yield: 16.9%), m.p. 110°–111° C.

NMR (CDCl$_3$) δ1.45 (6H, s), 2.06 (3H, s), 2.09 (3H, s), 2.13 (3H, s), 2.94 (2H, s), 3.26 (2H, broad s).

EXAMPLE 104

2,2,4,6,7-Pentamethyl-5-phenylamino-2,3-dihydrobenzofuran

To a solution of 3,5,6-trimethyl-2-(2-methyl-2-propenyl)-4-phenylaminophenol (1.40 g, 4.98 mmol) in methanol (30 ml) was added conc. hydrochloric acid (10 ml) with ice-cooling and the mixture was heated with reflux in an argon atmosphere. The reaction mixture was cooled, neutralized with an aqueous sodium bicarbonate solution and extracted with ethyl acetate. The extract was washed with a saturated saline solution and concentrated. The residue was recrystallized from isopropyl ether to obtain the desired compound (0.97 g, yield: 69.3%), m.p. 148°–150° C.

NMR (CDCl$_3$) δ1.49 (6H, s), 2.04 (3H, s), 2.10 (3H, s), 2.12 (3H, s), 2.95 (2H, s), 5.03 (1H, broad s), 6.42–6.48 (2H, m), 6.64–6.72 (1H, m), 7.08–7.17 (2H, m).

EXAMPLE 105

5-(4-Chlorophenylamino)-2,2,4,6,7-pentamethyl-2,3-dihydrobenzofuran

According to the same manner as that described in Example 104, the titled compound was obtained (yield: 60.0%), m.p. 106°–107° C. (isopropyl ether-pentane).

NMR (CDCl$_3$) δ1.49 (6H, s), 2.02 (3H, s), 2.07 (3H, s), 2.12 (3H, s), 2.95 (21i, s), 5.04 (1H, broad s), 6.36 (2H, d, J=8.8 Hz), 7.06 (2H, d, J=8.8 Hz).

EXAMPLE 106

5-(4-Methoxyphenylamino)-2,2,4,6,7-pentamethyl-2,3-dihydrobenzofuran

According to the same manner as that described in Example 104, the titled compound was obtained (yield: 61.2%), m.p. 117°–119° C. (isopropyl ether-pentane).

NMR (CDCl$_3$) δ1.49 (6H, s), 2.04 (3H, s), 2.09 (3H, s), 2.12 (3H, s), 2.95 (2H, s), 3.73 (3H, s), 4.86 (1H, broad s), 6.41 (2H, d, J=9.0 Hz), 6.73 (2H, d, J=9.0 Hz).

Reference Example 1

4-Amino-2,3,5-trimethylphenol

Solid Na$_2$CO$_3$ (13.7 g, 129 mmol) was added slowly with stirring at room temperature to a solution of sulfanilic acid (49.4 g, 258 mmol) in water (250 ml). After the reaction mixture became a homogeneous solution (when the mixture could not be dissolved at the temperature, it could be heated a little), the mixture was cooled with ice and a solution of NaNO$_2$ (19.4 g, 280 mmol) in water (50 ml) was added at an inner temperature of below 10° C. Then, this solution was placed in a dropping funnel. The solution was added dropwise to a mixture of concentrated hydrochloric acid (46 ml) and ice (100 g) over about 10 minutes with stirring under ice cooling at an inner temperature of the dropping funnel of below 10° C. After the addition was completed, the reaction mixture was stirred for 30 minutes under ice cooling. Next, water (250 ml), NaOH (56.8 g, 142 mmol) and 2,3,5-trimethylphenol (35.3 g, 259 mmol) were placed in another reaction vessel equipped with a mechanical stirring apparatus and to this mixture was added dropwise the reaction mixture above with stirring under a stream of nitrogen over 15 minutes in the range of −10° C. to 5° C. At that time ice was properly added to the ice bath to cool the reaction system in order to keep a temperature of the contents in the dropping funnel below 10° C. After the addition was completed, the reaction mixture was heated to 50° C. and Na$_2$S$_2$O$_4$ (11.9 g, 68.3 mmol) was added. Then the mixture was heated to 80° C. and further 5 equal parts of Na$_2$S$_2$O$_4$ (214.2 g, 1.23 mol) were added at intervals of 5 minutes. The reaction mixture was stirred for 30 minutes at the same temperature and then cooled. The precipitated crystals were filtered. The crystals obtained were washed with water, dried and then recrystallized from ethyl acetate-isopropyl ether to obtain the desired compound (33.0 g, yield: 84.2%), m.p. 153°–154° C.

NMR (CDCl$_3$) δ2.11 (6H, s), 2.16 (3H, s), 3.55 (3H, broad s), 6.42 (2H, s).

Reference Example 2

4-Amino-2,5-dimethylphenol

The title compound was synthesized according to the same manner as that described above (yield: 59.7%) m.p. 216°–220° C. (water).

NMR (DMSO-d$_6$) δ1.94 (3H, s), 1.97 (3H, s), 4.06 (2H, broad s), 6.33 (1H, s), 6.38 (1H, s), 8.04 (1H, s).

Reference Example 3

4-Amino-3,5-dimethylphenol

The title compound was synthesized according to the same manner as that described above (yield: 52.2%), m.p. 190°–191° C. (water).

NMR (DMSO-d$_6$) δ2.01 (6H, s), 3.90 (2H, broad s), 6.28 (2H, s), 8.19 (1H, s).

Reference Example 4

4-Formylamino-2,3,5-trimethylphenol

4-Amino-2,3,5-trimethylphenol (100 g, 662 mmol) was dissolved in formic acid (500 ml). The mixture was heated under reflux for 36 hours. The reaction mixture was poured into ice-cold water. The precipitated crystals were filtered, washed with water and dried. The crude crystals obtained were recrystallized from ethanol to obtain the desired compound (85.9 g, yield: 72.5%), m.p. 219°–220° C.

NMR (CDCl$_3$) δ2.00 (3H, s), 2.03 (6H, s), 6.53 (1H, s), 8.20 (1H, d, J=1.8 Hz), 9.06 (1H, s), 9.15 (1H, broad s).

Reference Example 5

4-Formylamino-3,5-dimethylphenol

The title compound was synthesized according to the same manner as that described above (yield: 70.3%), m.p. 239° C. (dichloromethane-isopropyl ether).

NMR (DMSO-d$_6$) δ2.05 (6H, s), 6.46 (2H, s), 8.19 (1H, s), 9.13 (1H, broad s), 9.16 (1H, s).

Reference Example 6

1-Acetoxy-4-acetylamino-2,3,5-trimethylbenzene

4-Amino-2,3,5-trimethylphenol (26.5 g, 17.5 mmol) was dissolved in pyridine (80 ml). Acetic anhydride (53 ml, 56.2 mmol) was added to the solution with stirring. After the reaction mixture was stirred for 1 hour, the mixture was poured into ice-cold water and crystals precipitated were filtered. The crystals were washed with water, dried and then recrystallized from ethyl acetate to obtain the desired compound (36.5 9, yield: 88.5%), m.p. 174°–175° C.

NMR (CDCl$_3$) δ2.00–2.25 (12H, m), 2.31 (3H, s), 6.60–6.90 (2H, m).

Reference Example 7

1-Acetoxy-4-acetylamino-2,3-dimethylbenzene

The title compound was synthesized according to the same manner as that described above (yield: 88.3%), m.p. 155°–156° C. (dichloromethane-isopropyl ether).

NMR (CDCl$_3$) δ2.09 (3H, s), 2.14 (3H, s), 2.19 (3H, s), 2.33 (2H, s), 6.86 (1H, d, J=8.5 Hz), 7.05 (1H, broad s), 7.37 (1H, d, J=8.5 Hz).

Reference Example 8

1-Acetoxy-4-acetylamino-2,5-dimethylbenzene

The title compound was synthesized according to the same manner as that described above (yield: 54.9%), m.p. 177° C. (dichloromethane-isopropyl ether)

NMR (CDCl$_3$) δ2.12 (3H, s), 2.16 (3H, s), 2.30 (3H, s), 6.81 (1H, s), 7.02 (1H, broad s), 7.57 (1H, s).

Reference Example 9

4-Acetylamino-2,3,5-trimethylphenol

A solution of potassium carbonate (27 g, 195 mmol) in water (150 ml) was added to a solution of 1-acetoxy-4-acetylamino-2,3,5-trimethylbenzene (66.0 g, 324 mmol) in methanol (300 ml) and the mixture was stirred for 1 hour under an argon atmosphere. Aqueous 1N hydrochloric acid solution was added to the reaction mixture to make the mixture weak acid and the resulting mixture was diluted with water. Crystals precipitated were filtered, washed with water, dried and then recrystallized from ethyl acetate-isopropyl ether to obtain the desired compound (36.8 g, yield: 67.9%), m.p. 189°–190° C. (ethyl acetate-isopropyl ether).

NMR (DMSO-d$_6$) δ1.98 (3H, s), 1.99 (6H, s), 2.01 (3H, s), 6.50 (1H, s), 8.95 (1H, s), 9.00 (1H, s).

Reference Example 10

4-Acetylamino-2,3-dimethylphenol

The title compound was synthesized according to the same manner as that described above (yield: 40.0%), m.p. 184°–185° C. (dichloromethane-isopropyl ether).

NMR (CDCl$_3$) δ2.13 (3H, s), 2.16 (3H, s), 2.18 (3H, s), 6.66 (1H, d, J=8.5 Hz), 7.01 (1H, d, J=8.5 Hz), 7.22 (1H, broad s), 7.29 (1H, s).

Reference Example 11

4-Acetylamino-2,5-dimethylphenol

The title compound was synthesized according to the same manner as that described above (yield: 92.1%), m.p. 183° C. (dichloromethane-isopropyl ether).

NMR (DMSO-d$_6$) δ1.97 (3H, s), 2.04 (6H, s), 6.58 (1H, s), 6.91 (1H, s), 9.03 (2H, s).

Reference Example 12

4-Formylamino-2,3,5-trimethyl-1-(2-methyl-2-propenyloxy)benzene

Potassium carbonate (74.0 g, 0.54 mol) was added to a solution of 4-formylamino-2,3,5-trimethylphenol (85.5 g, 0.48 mol) and methallyl chloride (45.3 g, 0.5 mol) in dimethylformamide (300 ml) and the mixture was stirred at 80° C. for 3 hours under an argon atmosphere. The reaction mixture was poured into ice-cold water. Crystals precipitated were filtered, washed with water and dried. The crude crystals obtained were recrystallized from isopropyl ether to obtain the desired compound (80.0 g, yield: 71.6%), m.p. 144°–145° C.

NMR (CDCl$_3$) δ1.84 (3H, m), 2.17 (3H, s), 2.19 (1.5H, s), 2.22 (3H, s), 2.26 (1.5H, s), 4.40 (1H, s), 4.42 (1H, s), 4.99 (1H, m), 5.11 (1H, broad s), 6.60 (1H, s), 6.75 (1H, m), 7.98 (0.5H, d, J=12.0 Hz), 8.41 (0.5H, s).

Reference Example 13

4-Acetylamino-2,3,5-trimethyl-1-(2-methyl-2-propenyloxy)benzene

The title compound was synthesized according to the same manner as that described above (yield: 92.6%), m.p. 149°–150° C. (isopropyl ether).

NMR (CDCl$_3$) δ1.84 and 1.86 (3H, s), 2.14 (3H, s), 2.16 (3H, s), 2.19 (3H, s), 2.20 (3H, s), 4.38 and 4.32 (2H, s), 4.98 (1H, m), 5.11 (1H, broad s), 6.58 and 6.50 (1H, s), 6.60 and 6.72 (1H, broad s).

Reference Example 14

2,3,5-Trimethyl-1-(2-methyl-2-propenyloxy)benzene

The title compound was synthesized according to the same manner as that described above (yield: 98.9%), b.p. 108°–112° C. (10 mmHg).

NMR (CDCl$_3$) δ1.87 (3H, s), 2.17 (3H, s), 2.26 (3H, s), 2.30 (3H, s), 4.42 (2H, s), 5.00 (1H, broad s), 5.15 (1H, broad s), 6.55 (1H, broad s), 6.64 (1H, broad s).

Reference Example 15

4-Acetylamino-2,3-dimethyl-1-(2-methyl-2-propenyloxy)benzene

The title compound was synthesized according to the same manner as that described above (yield: 86.2%), m.p. 154°–156° C. (dichloromethane-isopropyl ether).

NMR (CDCl$_3$) δ1.84 (3H, s), 2.16 (3H, s), 2.19 (3H, s), 2.21 (3H, s), 4.41 (2H, s), 4.98 (1H, s), 5.12 (1H, s), 6.70 (1H, d, J=8.8 Hz), 6.89 (1H, broad s), 7.20 (1H, d, J=8.8 Hz).

Reference Example 16

4-Acetylamino-2,5-dimethyl-1-(2-methyl-2-propenyloxy)benzene

The title compound was synthesized according to the same manner as that described above (yield: 84.3%), m.p. 128°–132° C. (dichloromethane-isopropyl ether).

NMR (CDCl$_3$) δ1.60 and 2.17 (3H, s), 1.84 (3H, s), 2.20 (6H, s), 4.40 (2H, s), 4.98 (1H, s), 5.11 (1H, s), 6.63 (1H, s), 6.80 (1H, broad s), 7.28 (1H, s).

Reference Example 17

4-Formylamino-3,5-dimethyl-1-(2-methyl-2-propenyloxy)benzene

The title compound was synthesized according to the same manner as that described above (yield: 98.4%), m.p. 128°–129° C. (isopropyl ether).

NMR (DMSO-d$_6$) δ1.77 (3H, s), 2.11 (6H, s), 4.43 (2H, s), 4.95 (1H, s), 5.05 (1H, s), 6.68 (2H, s), 8.22 (1H, s), 9.26 (1H, s).

Reference Example 18

4-Formylamino-3,5-dimethyl-2-(2-methyl-2-propenyl)-1-(2-methyl-2-propenyloxy)benzene The title compound was synthesized according to the same manner as that described above (yield: 98.4%), m.p. 109° C. (dichloromethane-isopropyl ether).

NMR (DMSO-d$_6$) δ1.72 (3H, s), 1.76 (3H, s), 2.01 (3H, s), 2.12 (3H, s), 3.32 (2H, s), 4.30 (1H, s), 4.41 (2H, s), 4.66 (1H, s), 4.93 (1H, s), 5.06 (1H, s), 6.73 (1H, s), 8.22 (1H, s), 9.27 (1H, s).

Reference Example 19

4-Formylamino-2,3,5-trimethyl-6-(2-methyl-2-propenyl)phenol

4-Formylamino-2,3,5-trimethyl-1-(2-methyl-2-propenyloxy benzene (80 9, 0.34 mol) was dissolved in N,N-diethylaniline (500 ml). The solution was heated at 200° C. for 3 hours. The solution was allowed to cool. When crystals were precipitated, hexane was added. The crystals precipitated were filtered to obtain the desired compound (75.2 g, yield: 94.0%). The crude crystals were recrystallized from ethyl acetate-isopropyl ether to obtain crystals, m.p. 163°–164° C.

NMR (CDCl$_3$) δ1.80 (3H, s), 2.16 (3H, s), 2.17 (1.5H, s), 2.19 (1.5H, s), 2.20 (1.5H, s), 2.21 (1.5H, s), 3.38 (2H, broad s), 4.65 (1H, m), 4.88 (1H, m), 5.16 (0.5H, s), 5.19 (0.5H, s), 6.70 (1H, m), 7.95 (0.5H, d, J=12.0 Hz), 8.42 (0.5H, d, J=1.8 Hz).

Reference Example 20

4-Acetylamino-2,3,5-trimethyl-6-(2-methyl-2-propenyl)phenol

The title compound was synthesized according to the same manner as that described above (yield: 97.7%), m.p. 209°–210° C. (ethyl acetate-isopropyl ether).

NMR (CDCl$_3$) δ1.73 (3H, s), 1.94 (3H, s), 1.99 (6H, s), 2.09 (3H, s), 3.33 (2H, m), 4.28 (1H, broad s), 4.64 (1H, broad s), 7.86 (1H, broad s), 9.00 (1H, s).

Reference Example 21

2,3,5-Trimethyl-6-(2-methyl-2-propenyl)phenol

The title compound was synthesized according to the same manner as that described above (yield: 80.6%) b.p. 124°–126° C. (10 mmHg).

NMR (CDCl$_3$) δ1.79 (3H, s), 2.14 (3H, s), 2.24 (6H, s), 3.37 (2H, s), 4.74 (1H, m), 4.88 (1H, m), 5.08 (1H, s), 6.63 (1H, s).

Reference Example 22

4-Acetylamino-2,3-dimethyl-6-(2-methyl-2-propenyl)phenol

The title compound was synthesized according to the same manner as that described above (yield: 91.8%), m.p. 149°–151° C. (dichloromethane-isopropyl ether).

NMR (CDCl$_3$) δ1.72 (3H, s), 2.12 (3H, s), 2.16 (3H, s), 2.17 (3H, s), 3.32 (2H, s), 4.89–4.94 (2H, m), 5.39 (1H, s), 6.92 (1H, broad s), 7.00 (1H, s).

Reference Example 23

4-Acetylamino-2,5-dimethyl-6-(2-methyl-2-propenyl)phenol

The title compound was synthesized according to the same manner as that described above (yield: 98.7%), m.p. 183°–185° C. (dichloromethane-isopropyl ether).

NMR (CDCl$_3$) δ1.79 (3H, s), 2.11–2.22 (9H, m), 3.38 (2H, s), 4.60 (1H, s), 4.83 (1H, s), 7.11 (1H, s).

Reference Example 24

4-Formylamino-3,5-dimethyl-2-(2-methyl-2-propenyl)phenol

The title compound was synthesized according to the same manner as that described above (yield: 80.8%), m.p. 207°–209° C. (isopropyl ether).

NMR (DMSO-d$_6$) δ1.71 (3H, s), 1.97 (3H, s), 2.04 (3H, s), 3.25 (2H, s), 4.33 (1H, s), 4.65 (1H, s), 6.55 (1H, s), 8.19 (1H, s), 9.09 (1H, s).

Reference Example 25

2,6-Bis(2-methyl-2-propenyl)-4-formylamino-3,5-dimethylphenol

The title compound was synthesized according to the same manner as that described above (yield: 84.2%), m.p. 169°–170° C. (isopropyl ether).

NMR (DMSO-d$_6$) δ1.72 (6H, s), 1.98 (6H, s), 3.33 (4H, s), 4.28 (2H, s), 4.65 (2H, s), 7.86 (1H, s), 8.20 (1H, s), 9.19 (1H, s).

Reference Example 26

2-Bromo-3,5,6-trimethylanisole

A solution of t-butylamine (73 g, 1.0 mol) in toluene (1 L) was cooled to −20° to 300° C. and bromine (79.9 g, 0.5 mol) was added dropwise over about 10 minutes. The reaction mixture was cooled to −70° to −75° C. and to this mixture was added dropwise 2,3,5-trimethylphenol (68 g, 0.5 mol) which was dissolved in the smallest amount of dichloromethane. The reaction mixture was stirred at the same temperature for 30 minutes and at room temperature for 3 hours. Then the mixture was washed with water, dried and concentrated. Sodium hydride (60% content, 22 g, 0.55 mol) was placed in another reaction vessel and washed with hexane 2 or 3 times, and then dimethylformamide (500 ml) was added. A solution of the concentrated residue above in dimethylformamide (50 ml) was added to the mixture. The reaction mixture was stirred for 30 minutes and iodomethane (34.2 ml, 0.55 mol) was added dropwise. The resulting mixture was stirred for additional 1 hour. The reaction mixture was diluted with water and the product was extracted with isopropyl ether. The extract was washed with water, dried and then concentrated. The concentrated residue was distilled under reduced pressure. The fractions having boiling point of 130° to 135° C. were collected to obtain the desired compound (32.3 g, yield: 28.6%).

NMR (CDCl$_3$) δ2.20 (3H, s), 2.21 (3H, s), 2.34 (3H, s), 3.76 (3H, s), 6.83 (1H, s).

Reference Example 27

1-(2-Methoxy-3,4,6-trimethylphenyl)-1-phenyl-2-methylpropanol

A solution of 2-bromo-3,5,6-trimethylanisole (3.0 g, 13.1 mmol) in tetrahydrofuran (20 ml) was cooled to −78° C. and n-butyllithium (1.6M solution in hexane, 8.2 ml, 13.1 mmol) was added dropwise. The reaction mixture was stirred at the same temperature for 15 minutes. Then a solution of isobutyrylbenzene (1.94 g, 13.1 mmol) in tetrahydrofuran (5 ml) was added dropwise and the resulting mixture was stirred at room temperature for additional 30 minutes. The reaction mixture was diluted with water and the product was extracted with isopropyl ether. The extract was washed with water, dried and then concentrated. The residue was crystallized from hexane to obtain the desired compound (3.13 9, yield: 80.2%), m.p. 80°–81° C.

NMR (CDCl$_3$) δ0.88 (3H, d, J=6.6 Hz), 1.05 (3H, d, J=6.4 Hz), 2.07 (3H, s), 2.18 (3H, s), 2.58 (3H, s), 2.82 (1H, qq, J=6.4 Hz and 6.6 Hz), 2.90 (3H, s), 6.18 (1H, broad s), 6.75 (1H, s), 7.10–7.30 (3H, m), 7.40–7.50 (2H, m).

Reference Example 28

1-(4-Fluorophenyl)-1-(2-methoxy-3,4,6-trimethylphenyl)-2-methylpropanol

The title compound was synthesized according to the same manner as that described above (yield: 97.9%), m.p. 102°–103° C. (hexane).

NMR (CDCl$_3$) δ0.88 (3H, d, J=6.6 Hz), 1.02 (3H, d, J=6.4 Hz), 2.08 (3H, s), 2.19 (3H, s), 2.53 (3H, s), 2.80 (1H, qq, J=6.4 Hz and 6.6 Hz), 2.97 (3H, s), 6.23 (1H, broad s), 6.75 (1H, s), 6.95 (2H, t, J=8.8 Hz), 7.40 (2H, dd, J=8.8 Hz and 5.4 Hz).

Reference Example 29

1-(2-Methoxy-3,4,6-trimethylphenyl)-1-(4-methylphenyl)-2-methylpropanol

The title compound was synthesized according to the same manner as that described above (yield: 80.6%), m.p. 103°–104° C. (hexane).

NMR (CDCl$_3$) δ0.89 (3H, d, J=6.6 Hz), 1.03 (3H, d, J=6.4 Hz), 2.09 (3H, s), 2.19 (3H, s), 2.30 (3H, s), 2.56 (3H, s), 2.82 (1H, qq, J=6.4 Hz and 6.6 Hz), 2.95 (3H, s), 6.18 (1H, broad s), 6.75 (1H, s), 7.07 (2H, d, J=8.2 Hz), 7.32 (2H, d, J=8.2 Hz).

Reference Example 30

1-(2-Methoxy-3,4,6-trimethylphenyl)-1(4-propylphenyl)-2-methylpropanol

The title compound was synthesized according to the same manner as that described above (yield: 74.6%), m.p. 59°–60° C. (hexane).

NMR (CDCl$_3$) δ0.87 (3H, t, J=6.4 Hz), 0.90 (3H, d, J=6.6 Hz), 1.03 (3H, d, J=6.4 Hz), 1.60 (2H, sextet, 6.4 Hz), 2.08 (3H, s), 2.18 (3H, s), 2.54 (2H, t, J=6.4 Hz), 2.56 (3H, s), 2.84 (1H, qq, J=6.6 Hz and 6.4 Hz), 2.93 (3H, s), 6.15 (1H, broad s), 7.06 (2H, d, J=8.4 Hz), 7.33 (2H, d, J=8.4 Hz).

Reference Example 31

1-(2-Methoxy-3,4,6-trimethylphenyl)-1-(4-pentylphenyl)-2-methylpropanol

The title compound was synthesized according to the same manner as that described above (yield: 75.4%), m.p. 55°–56° C. (hexane).

NMR (CDCl$_3$) δ0.85 (3H, t, J=6.2 Hz), 0.90 (3H, d, J=6.6 Hz), 1.03 (3H, d, J=6.6 Hz), 1.28 (4H, m), 1.56 (2H, quintet, J=6.8 Hz), 2.08 (3H, s), 2.18 (3H, s), 2.54 (2H, t, J=7.5 Hz), 2.55 (3H, s), 2.84 (1H, septet, J=6.6 Hz), 2.92 (3H, s), 6.15 (1H, broad s), 6.75 (1H, s), 7.07 (2H, d, J=8.0 Hz), 7.34 (2H, d, J=8.0 Hz).

Reference Example 32

1-(4-Isopropylphenyl)-1-(2-methoxy-3,4,6-trimethylphenyl)-2-methylpropanol

The title compound was synthesized as oil according to the same manner as that described above (yield: 65.1%).

NMR (CDCl$_3$) δ0.91 (3H, d, J=6.6 Hz), 1.02 (3H, d, J=6.6 Hz), 1.20 (6H, d, J=7.0 Hz), 2.08 (3H, s), 2.17 (3H, s), 2.54 (3H, s), 2.84 (1H, septet, J=6.6 Hz), 2.93 (3H, s), 2.96 (1H, septet, J=7.0 Hz), 6.16 (1H, broad s), 6.74 (1H, s), 7.10 (2H, d, J=8.4 Hz), 7.90 (2H, d, J=8.4 Hz).

Reference Example 33

1-(2-Methoxy-3,4,6-trimethylphenyl)-1-(3-pyridyl)-2-methylpropanol

The title compound was synthesized as oil according to the same manner as that described above (yield: 68.9%).

NMR (CDCl$_3$) δ0.93 (3H, d, J=6.6 Hz), 1.03 (3H, d, J=6.6 Hz), 2.09 (3H, s), 2.19 (3H, s), 2.51 (3H, s), 2.90 (1H, septet, J=6.6 Hz), 3.05 (3H, s), 6.29 (1H, broad s), 6.76 (1H, s), 7.22 (1H, dd, J=4.8 Hz and 8.0 Hz), 7.79 (1H, dt, J=2.0 Hz and 8.0 Hz), 8.43 (1H, dd, J=2.0 Hz and 4.8 Hz), 8.70 (1H, d, J=2.0 Hz).

Reference Example 34

1-(2-Methoxy-3,4,6-trimethyl)-1-(4-dimethylaminophenyl)-2-methylpropanol

The title compound was synthesized according to the same manner as that described above (yield: 59.1%), m.p. 95°–97° C. (hexane).

NMR (CDCl$_3$) δ0.93 (3H, d, J=6.6 Hz), 1.00 (3H, d, J=6.4 Hz), 2.08 (3H, s), 2.18 (3H, s), 2.53 (3H, s), 2.82 (1H, qq, J=6.4 Hz and 6.6 Hz), 2.90 (6H, s), 2.99 (3H, s), 6.12 (1H, broad s), 6.66 (2H, d, J=9.0 Hz), 6.74 (1H, s), 7.28 (2H, d, J=9.0 Hz).

Reference Example 35

3-(2-Methoxy-3,4,6-trimethylphenyl)-2,4-dimethylpentan-3-ol

The title compound was synthesized as oil according to the same manner as that described above (yield: 11.6%).

NMR (CDCl$_3$) δ0.78 (6H, d, J=6.6 Hz), 1.03 (6H, d, J=6.6 Hz), 2.15 (3H, s), 2.19 (3H, s), 2.42 (3H, s), 2.45 (2H, septet, J=6.6 Hz), 3.73 (3H, s), 6.75 (1H, s), 6.88 (1H, s).

Reference Example 36

5-Acetylamino-2,2,6,7-tetramethyl-2,3-dihydrobenzofuran

The title compound was synthesized according to the same manner as that described in Example 3 (yield: 71.9%), m.p. 163°–164° C. (ethanol).

NMR (CDCl$_3$) δ1.45 (6H, s), 2.10 (3H, s), 2.11 (3H, s), 2.17 (3H, s), 2.98 (2H, s), 7.00 (1H, s), 7.33 (1H, broad s).

Reference Example 37

5-Acetylamino-2,2,4,7-tetramethyl-2,3-dihydrobenzofuran

The title compound was synthesized according to the same manner as that described above (yield: 67.3%), m.p. 161°–162° C. (isopropyl ether).

NMR (CDCl$_3$) δ1.47 (6H, s), 2.06 (3H, s), 2.13 (3H, s), 2.14 (3H, s), 2.93 (2H, s), 6.81 (1H, broad s), 6.95 (1H, s).

Reference Example 38

5-Amino-2,2,4,6-tetramethyl-2,3-dihydrobenzofuran hydrochloride

The title compound was synthesized according to the same manner as that described above (yield: 43.0%), m.p. 215°–217° C. (isopropanol).

NMR (DMSO-d$_6$) δ1.40 (6H, s), 2.22 (3H, s), 2.29 (3H, s), 2.94 (2H, s), 6.49 (1H, s), 9.58 (2H, broad s).

Reference Example 39

5-Amino-2,2,6,7-tetramethyl-2,3-dihydrobenzofuran hydrochloride

The title compound was synthesized according to the same manner as that described above (yield: 38.7%), m.p. 235°–238° C. (ethanol).

NMR (CDCl$_3$) δ1.45 (6H, s), 2.13 (3H, s), 2.40 (3H, s), 2.97 (2H, s), 7.27 (2H, s), 10.23 (2H, broad s).

Reference Example 40

2,2,4,6,7-Pentamethyl-3-phenyl-2,3-dihydrobenzofuran 1-(2-Methoxy-3,4,6-trimethylphenyl)-1-phenyl-2-methylpropanol (3.1 g, 10.4 mmol) was suspended in 48% hydrobromic acid (20 ml). The suspension was heated under reflux for 18 hours. The product was extracted with isopropyl ether, washed with water, dried and then concentrated. The residue was crystallized from ethanol to obtain the desired compound (2.43 g, yield: 87.8%), m.p. 86°–87° C.

NMR (CDCl$_3$) δ1.02 (3H, s), 1.51 (3H, s), 1.84 (3H, s), 2.15 (3H, s), 2.24 (3H, s), 4.13 (1H, s), 6.49 (1H, s), 6.70–7.40 (5H, m).

Reference Example 41

3-(4-Fluorophenyl)-2,2,4,6,7-pentamethyl-2,3-dihydrobenzofuran

The title compound was synthesized according to the same manner as that described above (yield: 83.5%), m.p. 109°–110° C. (methanol).

NMR (CDCl$_3$) δ1.02 (3H, s), 1.49 (3H, s), 1.83 (3H, s), 2.14 (3H, s), 2.24 (3H, s), 4.10 (1H, s), 6.49 (1H, s), 6.60–7.20 (4H, m).

Reference Example 42

2,2,4,6,7-Pentamethyl-3-(4-methylphenyl)-2,3-dihydrobenzofuran

The title compound was synthesized according to the same manner as that described above (yield: 87.7%), m.p. 117°–118° C. (methanol).

NMR (CDCl$_3$) δ1.02 (3H, s), 1.50 (3H, s), 1.85 (3H, s), 2.15 (3H, s), 2.24 (3H, s), 2.31 (3H, s), 4.10 (1H, s), 6.49 (1H, s), 6.50–7.20 (4H, m).

Reference Example 43

2,2,4,6,7-Pentamethyl-3-(4-propylphenyl)-2,3-dihydrobenzofuran

The title compound was synthesized according to the same manner as that described above (yield: 84.9%), m.p. 69°–70° C. (methanol).

NMR (CDCl$_3$) δ0.90 (3H, t, J=7.2 Hz), 1.02 (3H, s), 1.50 (3H, s), 1.61 (2H, sextet, J=8.0 Hz), 1.84 (3H, s), 2.15 (3H, s), 2.24 (3H, s), 2.55 (2H, t, J=8.0 Hz), 4.10 (1H, s), 6.49 (1H, s), 6.60–7.20 (4H, m).

Reference Example 44

2,2,4,6,7-Pentamethyl-3-(4-pentylphenyl)-2,3-dihydrobenzofuran

The title compound was synthesized as oil according to the same manner as that described above (yield: 70.7%).

NMR (CDCl$_3$) δ0.88 (3H, t, J=4.6 Hz), 1.03 (3H, s), 1.30 (4H, m), 1.50 (3H, s), 1.56 (2H, m), 1.85 (3H, s), 2.15 (3H, s), 2.24 (3H, s), 2.56 (2H, t, J=8.0 Hz), 4.10 (1H, s), 6.45 (1H, s), 6.60–7.20 (4H, m).

Reference Example 45

3-(4-Isopropylphenyl)-2,2,4,6,7-pentamethyl-2,3-dihydrobenzofuran

The title compound was synthesized as oil according to the same manner as that described above (yield: 65.1%).

NMR (CDCl$_3$) δ1.02 (3H, s), 1.21 (6H, d, J=7.0 Hz), 1.49 (3H, s), 1.84 (3H, s), 2.14 (3H, s), 2.24 (3H, s), 2.95 (1H, septet, J=7.0 Hz), 4.09 (1H, s), 6.48 (1H, s), 6.70–7.20 (4H, m).

Reference Example 46

2,2,4,6,7-Pentamethyl-3-(3-pyridyl)-2,3-dihydrobenzofuran

The title compound was synthesized as oil according to the same manner as that described above (yield: 77.1%).

NMR (CDCl$_3$) δ1.05 (3H, s), 1.53 (3H, s), 1.84 (3H, s), 2.14 (3H, s), 2.24 (3H, s), 4.14 (1H, s), 6.50 (1H, s), 7.18 (2H, m), 8.35 (1H, m), 8.48 (1H, t, J=3.2 Hz).

Reference Example 47

2,2,4,6,7-Pentamethyl-3-(4-dimethylaminophenyl)-2,3-dihydrobenzofuran

The title compound was synthesized according to the same manner as that described above (yield: 88.1%), m.p. 124°–125° C. (methanol)

NMR (CDCl$_3$) δ1.03 (3H, s), 1.48 (3H, s), 1.85 (3H, s), 2.14 (3H, s), 2.23 (3H, s), 2.91 (6H, s), 4.04 (1H, s), 6.47 (1H, s), 6.55–7.00 (4H, m).

Reference Example 48

3-(4-Isopropyl)-2,2,4,6,7-pentamethyl-2,3-dihydrobenzofuran

The title compound was synthesized as oil according to the same manner as that described above (yield: 88.2%).

NMR (CDCl$_3$) δ0.73 (3H, d, J=6.8 Hz), 0.98 (3H, d, J=7.2 Hz), 1.21 (3H, s), 1.57 (3H, s), 2.06 (3H, s), 2.10 (1H, m), 2.20 (3H, s), 2.22 (3H, s), 2.73 (1H, d, J=2.8 Hz), 6.49 (1H, s).

Reference Example 49

2,2,4,5,6-Pentamethyl-7-nitro-2,3-dihydrobenzofuran

The mixed solution of acetic anhydride (5 ml) and acetic acid (5 ml) was cooled and nitric acid (5 ml) was added cautiously with stirring. Then, a solution of 2,2,4,5,6-pentamethyl-2,3-dihydrobenzofuran (2.9 g, 13.9 mmol) in acetic anhydride (5 ml) was added dropwise and the mixture was stirred for 30 minutes. The reaction mixture was poured into ice-cold water and the product was extracted with ethyl acetate. The extract was washed with saturated sodium bicarbonate solution, dried and concentrated. The residue was purified by column chromatography on silica gel (hexane-isopropyl ether, 9:1) and crystallized from methanol to obtain the desired compound (0.35 g, yield: 9.8% yield), m.p. 100°–101° C.

NMR (CDCl$_3$) δ1.51 (6H, s), 2.14 (3H, s), 2.17 (3H, s), 2.24 (3H, s), 2.99 (2H, s).

Reference Example 50

2,2,4,6,7-Pentamethyl-5-nitro-3-phenyl-2,3-dihydrobenzofuran

The mixed solution of acetic anhydride (3 ml) and acetic acid (3 ml) was cooled and nitric acid (3 ml) was added cautiously with stirring. Then a solution of 2,2,4,6,7-pentamethyl-3-phenyl-2,3-dihydrobenzofuran (3.7 g, 13.9 mmol) in acetic anhydride (3 ml) was added dropwise and the mixture was stirred for 30 minutes. The reaction mixture was poured into ice-cold water and the product was extracted with ethyl acetate. The extract was washed with saturated sodium bicarbonate solution, dried and concentrated. The residue was purified by column chromatography on silica gel (hexane-isopropyl ether, 9:1) and crystallized from methanol to obtain the desired compound (2.08 g, yield: 48.1%), m.p. 155°–156° C.

NMR (CDCl$_3$) δ1.04 (3H, s), 1.52 (3H, s), 1.83 (3H, s), 2.18 (3H, s), 2.20 (3H, s), 4.15 (1H, s), 6.85 (2H, m), 7.26 (3H, m).

Reference Example 51

3-(4-Fluorophenyl)-2,2,4,6,7-pentamethyl-5-nitro-2,3-dihydrobenzofuran

The title compound was synthesized according to the same manner as that described above (yield: 66.3%), m.p. 94°–95° C. (methanol).

NMR (CDCl$_3$) δ1.04 (3H, s), 1.50 (3H, s), 1.84 (3H, s), 2.18 (3H, s), 2.20 (3H, s), 4.14 (1H, s), 6.50–7.20 (4H, m).

Reference Example 52

2,2,4,6,7-Pentamethyl-3-(4-methylphenyl)-5-nitro-2,3-dihydrobenzofuran

The title compound was synthesized as oil according to the same manner as that described above (yield: 56.0%).

NMR (CDCl$_3$) δ1.05 (3H, s), 1.50 (3H, s), 1.84 (3H, s), 2.18 (3H, s), 2.20 (3H, s), 2.32 (3H, s), 4.11 (1H, s), 6.50–7.20 (4H, m).

Reference Example 53

2,2,4,6,7-Pentamethyl-5-nitro-3-(4-propylphenyl)-2,3-dihydrobenzofuran

The title compound was synthesized as oil according to the same manner as that described above (yield: 65.8%).

NMR (CDCl$_3$) δ0.91 (3H, t, J=7.4 Hz), 1.04 (3H, s), 1.50 (3H, s), 1.61 (2H, sextet, J=7.4 Hz), 1.84 (3H, s), 2.18 (3H, s), 2.20 (3H, s), 2.55 (2H, t, J=7.4 Hz), 4.12 (1H, s), 6.50–7.20 (4H, m).

Reference Example 54

2,2,4,6,7-Pentamethyl-5-nitro-3-(4-pentylphenyl)-2,3-dihydrobenzofuran

The title compound was synthesized as oil according to the same manner as that described above (yield: 76.4%).

NMR (CDCl$_3$) δ0.89 (3H, t, J=6.6 Hz), 1.04 (3H, s), 1.30 (4H, m), 1.50 (3H, s), 1.59 (2H, m), 1.84 (3H, s), 2.18 (3H, s), 2.20 (3H, s), 2.56 (2H, t, J=7.8 Hz), 4.11 (1H, s), 5.50–7.20 (4H, m).

Reference Example 55

3-(4-Isopropylphenyl)-2,2,4,6,7-pentamethyl-5-nitro-2,3-dihydrobenzofuran

The title compound was synthesized according to the same manner as that described above (yield: 48.0%), m.p. 109°–110° C. (methanol).

NMR (CDCl$_3$) δ1.04 (3H, s), 1.22 (6H, d, J=6.8 Hz), 1.50 (3H, s), 1.84 (3H, s), 2.18 (3H, s), 2.20 (3H, s), 2.87 (1H, septet, J=6.8 Hz), 4.12 (1H, s), 6.60–7.20 (4H, m).

Reference Example 56

2,2,4,6,7-Pentamethyl-5-nitro-3-(3-pyridyl)-2,3-dihydrobenzofuran

The title compound was synthesized as oil according to the same manner as that described above (yield: 60.7%).

NMR (CDCl$_3$) δ1.07 (3H, s), 1.54 (3H, s), 1.84 (3H, s), 2.19 (3H, s), 2.21 (3H, s), 4.18 (1H, s), 7.05–7.35 (2H, m), 8.25–8.60 (2H, m).

Reference Example 57

2,2,4,6,7-Pentamethyl-3-(4-dimethylamino-3-nitrophenyl)-5-nitro-2,3-dihydrobenzofuran The title compound was synthesized as oil according to the same manner as that described above (yield: 24.2%).

NMR (CDCl$_3$) δ1.13 (3H, s), 1.51 (3H, s), 1.91 (3H, s), 2.19(3H, s), 2.21 (3H, s), 2.81 (6H, s), 4.12 (1H, s), 7.00–7.80 (3H, m).

Reference Example 58

3-Isopropyl-2,2,4,6,7-pentamethyl-5-nitro-2,3-dihydrobenzofuran

The title compound was synthesized as oil according to the same manner as that described above (yield: 62.0%).

NMR (CDCl$_3$) δ0.72 (3H, d, J=7.0 Hz), 0.98 (3H, d, J=7.2 Hz), 1.23 (3H, s), 1.59 (3H, s), 2.09 (1H, m), 2.10 (3H, s), 2.16 (3H, s), 2.21 (3H, s), 2.78 (1H, d, J=2.8 Hz).

Reference Example 59

2,4,6,7-Tetramethyl-5-nitro-2-piperidinomethyl-2,3-dihydrobenzofuran

The title compound was synthesized as oil according to the same manner as that described above (yield: 62.8%).

NMR (CDCl$_3$) δ1.30–1.60 (6H, m), 1.42 (3H, s), 2.08 (3H, s), 2.14 (6H, s), 2.50 (6H, m), 2.78 (1H, d, J=15.6 Hz), 3.18 (1H, d, J=15.6 Hz).

Reference Example 60

2,4,6,7-Tetramethyl-2-morpholinomethyl-5-nitro-2,3-dihydrobenzofuran

The title compound was synthesized as oil according to the same manner as that described above (yield: 59.0%).

NMR (CDCl$_3$) δ1.44 (3H, s), 2.07 (3H, s), 2.15 (6H, s), 2.57 (6H, m), 2.80 (1H, d, J=15.6 Hz), 3.21 (1H, d, J=15.6 Hz), 3.66 (4H, t, J=4.4 Hz).

Reference Example 61

2,4,6,7-Tetramethyl-2-[2-(dimethylamino)ethyl]-5-nitro-2,3-dihydrobenzofuran

The title compound was synthesized as oil according to the same manner as that described above (yield: 53.0%).

NMR (CDCl$_3$) δ1.44 (3H, s), 1.62 (2H, m), 2.10 (3H, s), 2.13 (3H, s), 2.15 (3H, s), 2.24 (6H, s), 2.40 (2H, m), 2.87 (1H, d, J=15.6 Hz), 3.06 (1H, d, J=15.6 Hz).

Reference Example 62

2,4,6,7-Tetramethyl-5-nitro-2-(2-piperidinoethyl)-2,3-dihydrobenzofuran

The title compound was synthesized according to the same manner as that described above (yield: 46.3%), m.p. 247°–250° C.

NMR (CDCl$_3$) δ1.50 (3H, s), 1.90 (2H, m), 2.08 (3H, s), 2.13 (3H, s), 2.14 (3H, s), 2.18 (4H, m), 2.40 (2H, m), 2.64 (2H, m), 2.97 (1H, d, J=15.6 Hz), 3.07 (2H, m), 3.17 (1H, d, J=15.6 Hz), 3.55 (2H, m).

Reference Example 63

2,2,4,5,6-Pentamethyl-2,3-dihydrobenzofuran 3,4,5-Trimethylphenol (5.0 g, 36.7 mmol) and 2-methyl-2-propenol (3.2 g, 44.0 mmol) were added to formic acid (50 ml). The mixture was heated under reflux for 3 hours. The reaction mixture was diluted with isopropyl ether, washed with water and saturated sodium bicarbonate solution, dried and concentrated. The residue was purified by column chromatography on silica gel (hexane-isopropyl ether, 97:3) to obtain the desired compound (2.9 g, yield: 41.5%) as oil.

NMR (CDCl$_3$) δ1.45 (6H, s), 2.09 (3H, s), 2.14 (3H, s), 2.23 (3H, s), 2.93 (2H, s), 6.44 (1H, s).

Reference Example 64

5-Bromo-2-bromomethyl-2,4,6,7-tetramethyl-2,3-dihydrobenzofuran

The title compound was synthesized according to the same manner as that described in Example 29 (yield: 67.7%), m.p. 60°–61° C. (methanol).

NMR (CDCl$_3$) δ1.61 (3H, s), 2.15 (3H, s), 2.27 (3H, s), 2.35 (3H, s), 2.67 (1H, d, J=15.6 Hz), 3.33 (1H, d, J=15.6 Hz), 3.51 (2H, s).

Reference Example 65

2-Bromomethyl-2,4,6,7-tetramethyl-2,3-dihydrobenzofuran

Triethylamine (5.0 ml, 35.6 mmol) was added to a solution of 5-bromo-2-bromomethyl-2,4,6,7-tetramethyl-2,3-dihydrobenzofuran (12.4 g, 35.6 mmol) in ethanol (100 ml). Catalytic hydrogenation decomposition reaction was carried out on 5% palladium carbon under a hydrogen atmosphere. After the completion of the reaction, the catalyst was filtered and the filtrate was concentrated. The residue was dissolved in isopropyl ether, washed with water, dried and the solvent was distilled off. The residue was crystallized from methanol to obtain the desired compound (8.84 g, yield: 92.2%), m.p. 39–40° C.

NMR (CDCl$_3$) δ1.63 (3H, s), 2.08 (3H, s), 2.17 (3H, s), 2.21 (3H, s), 2.92 (1H, d, J=15.8 Hz), 3.26 (1H, d, J=15.8 Hz), 3.48 (1H, d, J=15.6 Hz), 3.58 (1H, d, J=15.6 Hz), 6.53 (1H, s).

Reference Example 66

2,4,6,7-Tetramethyl-2-piperidinomethyl-2,3-dihydrobenzofuran

The title compound was synthesized as oil according to the same manner as that described in Example 57 (yield: 81.6%).

NMR (CDCl$_3$) δ1.30–1.60 (6H, m), 1.44 (3H, s), 2.05 (3H, s), 2.15 (3H, s), 2.19 (3H, s), 2.40–2.65 (6H, m), 2.76 (1H, d, J=15.2 Hz), 3.06 (1H, d, J=15.2 Hz), 6.47 (1H, s).

Reference Example 67

2,4,6,7-Tetramethyl-2-morpholinomethyl-2,3-dihydrobenzofuran

The title compound was synthesized as oil according to the same manner as that described above (yield: 99.8%).

NMR (CDCl$_3$) δ1.44 (3H, s), 2.04 (3H, s), 2.15 (3H, s), 2.19 (3H, s), 2.40–2.70 (6H, m), 2.79 (1H, d, J=15.4 Hz), 3.08 (1H, d, J=15.4 Hz), 3.67 (4H, t, J=4.6 Hz), 6.48 (1H, s).

Reference Example 68

2-Cyanomethyl-2,4,6,7-tetramethyl-2,3-dihydrobenzofuran

2-Bromomethyl-2,4,6,7-tetramethyl-2,3-dihydrobenzofuran (6.5 g, 18.6 mmol) was dissolved in dimethylsulfoxide (30 ml). Sodium cyanide (1.43 g, 88 mmol) was added and the resulting mixture was stirred at 80° C. for 18 hours. The reaction mixture was diluted with water and the product was extracted with ethyl acetate. The extract was washed with water, dried and concentrated. The residue was purified by column chromatography on silica gel (hexane-isopropyl ether, 2:1). The crude crystals obtained were recrystallized from methanol to obtain the desired compound (4.1 g, yield: 79.7%), m.p. 58°–59° C.

NMR (CDCl$_3$) δ1.66 (3H, s), 2.07 (3H, s), 2.16 (3H, s), 2.20 (3H, s), 2.68 (1H, d, J=10.8 Hz), 2.75 (1H, d, J=10.8 Hz), 3.00 (1H, d, J=15.8 Hz), 3.12 (1H, d, J=15.8 Hz), 6.54 (1H, s).

Reference Example 69

2,4,6,7-Tetramethyl-2,3-dihydrobenzofuran-2-yl acetic acid

A solution of sodium hydroxide (12.0 g, 300 mmol) in water (30 ml) was added to a solution of 2-cyanomethyl-2,4,6,7-tetramethyl-2,3-dihydrobenzofuran (6.9 9, 32.1 mmol) in methanol (30 ml) and the mixture was heated under reflux for 18 hours. The reaction mixture was made weakly acidic with 6N hydrochloric acid and the product was extracted with ethyl acetate. The extract was washed with water, dried and concentrated. The residue was crystallized from ethyl acetate-hexane to obtain the desired compound (6.0 g, yield: 79.9%), m.p. 139°–140° C.

NMR (DMSO-d$_6$) δ1.61 (3H, s), 2.07 (3H, s), 2.16 (3H, s), 2.21 (3H, s), 2.78 (1H, d, J=10.8 Hz), 2.85 (1H, d, J=10.8 Hz), 2.97 (1H, d, J=15.4 Hz), 3.21 (1H, d, J=15.4 Hz), 6.52 (1H, s), 8.50 (1H, broad s).

Reference Example 70

N,N-Dimethyl-2,4,6,7-tetramethyl-2,3-dihydrobenzofuran- 2-ylacetamide

To a solution of 2,4,6,7-tetramethyl-2,3-dihydrobenzofuran-2-yl acetic acid (3.0 g, 12.8 mmol) in dimethylformamide (30 ml) were added 1-hydroxy-1H-benzotriazole monohydrate (HOBt) (2.1 g, 14.1 mmol) and 1-ethyl-3-(3-dimethylaminopropyl) carbodiimide hydrochloride (WSC) (3.7 g, 19.2 mmol). The mixture was stirred at room temperature for 1 hour. Then, 50% dimethylamine aqueous solution (3 ml) was added and the resulting mixture was stirred for additional 30 minutes. The reaction mixture was diluted with water and the product was extracted with ethyl acetate. The extract was washed with water, dried and concentrated. The residue was purified by column chromatography on silica gel (isopropyl ether) to obtain the desired compound (3.1 g, yield: 92.6% yield) as oil.

NMR (CDCl$_3$) δ1.59 (3H, s), 2.07 (3H, s), 2.14 (3H, s), 2.20 (3H, s), 2.77 (1H, d, J=15.0 Hz), 2.88 (1H, d, J=15.0 Hz), 2.94 (3H, s), 3.00 (1H, d, J=15.8 Hz), 3.03 (3H, s), 3.27 (1H, d, J=15.8 Hz), 6.50 (1H, s).

Reference Example 71

(2,4,6,7-Tetramethyl-2,3-dihydrobenzofuran-2-yl)-acetyl-1-piperidine

The title compound was synthesized as oil according to the same manner as that described above (yield: 90.7%).

NMR (CDCl$_3$) δ1.55 (3H, s), 1.60 (6H, m), 2.06 (3H, s), 2.13 (3H, s), 2.19 (3H, s), 2.78 (1H, d, J=14.8 Hz), 2.90 (1H, d, J=14.8 Hz), 2.97 (1H, d, J=15.8 Hz), 3.24 (1H, d, J=15.8 Hz), 3.40–3.60 (4H, m), 6.50 (1H, s).

Reference Example 72

2,4,6,7-Tetramethyl-2-[2-(dimethylamino)ethyl]-2,3-dihydrobenzofuran

N,N-dimethyl-2,4,6,7-tetramethyl-2,3-dihydrobenzofuran-2-yl acetamide (3.1 g, 11.9 mmol) was dissolved in tetrahydrofuran (50 ml) and lithium aluminum hydride (0.45 g) was added slowly under cooling. The reaction mixture was stirred for 30 minutes at room temperature and then poured into ice-cold water. The product was extracted with ethyl acetate. The extract was washed with water, dried and concentrated. The residue was purified by column chromatography on silica gel (chloroform-methanol, 95:5) to obtain the desired compound (2.2 g, yield: 81.6%) as oil.

NMR (CDCl$_3$) δ1.42 (3H, s), 1.90 (2H, m), 2.06 (3H, s), 2.12 (3H, s), 2.19 (3H, s), 2.23 (6H, s), 2.40 (2H, m), 2.82 (1H, d, J=15.4 Hz), 3.00 (1H, d, J=15.4 Hz), 6.47 (1H, s).

Reference Example 73

2,4,6,7-Tetramethyl-2-(2-piperidinoethyl)-2,3-dihydrobenzofuran

The title compound was synthesized as oil according to the same manner as that described above (yield: 74.9%).

NMR (CDCl$_3$) δ1.42 (3H, s), 1.30–1.60 (6H, m), 1.90 (2H, m), 2.05 (3H, s), 2.12 (3H, s), 2.21 (3H, S), 2.40–2.60 (6H, m), 2.82 (1H, d, J=15.8 Hz), 3.00 (1H, d, J=15.8 Hz), 6.47 (1H, s).

Reference Example 74

4-(4-Chlorophenylimino)-3,5,6-trimethyl-2-(2-methyl-2-propenyl)-2,5-cyclohexadien-1-one Titanium tetrachloride (2.42 ml, 22.1 mmol) was added dropwise to a solution of pyridine (7.13 ml, 88.2 mmol) in 1,2-dichloroethane (40 ml) and, after completion of addition, the reaction mixture was heated under reflux for 20 minutes in an argon atmosphere. After cooling of the reaction mixture, to the mixture was added a solution of 3,5,6-trimethyl-2-(2-methyl-2-propenyl)-1,4-benzoquinone (3.00 g, 14.7 mmol) and p-chloroaniline (5.62 g, 44.1 mmol) in 1,2-dichloroethane (20 ml) and the mixture was stirred at 90° C. for 45 minutes in an argon atmosphere. The reaction mixture was cooled and filtered through Cerite and the filtrate was washed with a saturated saline solution, dried and concentrated. The residue was purified by silica gel column chromatography (hexane-ethyl acetate, 93:7) to obtain the desired compound as oil (4.43 g, yield: 96.0%).

NMR δ1.53–2.20 (12H, m), 3.21 (2H, s), 4.51 (1H, s), 4.74 (1H, s), 6.68 (2H, d, J=8.8 Hz), 7.30 (2H, d, J=8.8 Hz).

Reference Example 75

4-4-(Methoxyphenylimino)-3,5,6-trimethyl-2-(2-methyl-2-propenyl)-2,5-cyclohexadien-1-one According to the same manner as that described in Reference Example 74, the titled compound as oil was obtained (yield: 19.1%)

NMR (CDCl$_3$) δ1.50–1.60 (3H, m), 1.77 (3H, broad s), 1.95–2.03 (3H, m), 2.25 (3H, broad s), 3.16–3.25 (2H, m), 3.82 (3H, s), 4.46–4.58 (IS, m), 4.74 (1H, broad s), 6.72 (2H, d, J=9.0 Hz), 6.88 (2H, d, J=9.0 Hz).

Reference Example 76

4-(4-Chlorophenylamino)-3,5,6-trimethyl-2-(2-methyl-2-propenyl)phenol

To a solution of 4-(4-chlorophenylamino)-3,5,6-trimethyl-2-(2-methyl-2-propenyl)-2,5-cyclohexadine-1-one (4.40 g, 14.0 mmol) in tetrahydrofuran (20 ml) was added a solution of sodium hydrosulfite (24.4 g, 0.14 mol) in water (50 ml) and the mixture was stirred at room temperature for 30 minutes. After separation of the organic phase, the aqueous phase was extracted with ethyl acetate and the extract was combined with the organic phase. The mixture was washed with water and dried and the solvent was distilled off under reduced pressure. The residue was purified by silica gel column chromatography (hexane-ethyl acetate, 95:5) to obtain the desired compound as oil (4.30 g, yield: 97.2%).

NMR (CDCl$_3$) δ1.80 (3H, s), 2.11 (3H, s), 2.12 (3H, s), 2.19 (3H, s), 3.40 (2H, s), 4.68 (1H, s), 4.87 (1H, s), 5.04 (1H, s), 5.14 (1H, broad s), 6.34 (2H, d, J=8.8 Hz), 7.06 (2H, d, J=8.8 Hz).

Reference Example 77

4-(4-Methoxyphenylamino)-3,5,6-trimethyl-2-(2-methyl-2-propenyl)phenol

According to the same manner as that described in Reference Example 74, the titled compound as oil was obtained (yield: 98.2%).

NMR (CDCl$_3$) δ1.80 (3H, s), 2.14 (6H, s), 2.19 (3H, s), 3.40 (2H, s), 3.73 (3H, 8), 4.69 (1H, S), 4.85–5.05 (3H, m), 6.38 (2H, d, J=8.8 Hz), 6.73 (2H, d, J=8.8 Hz).

Reference Example 78

3,5,6-Trimethyl-2-(2-methyl-2-propenyl)-4-phenylaminophenol

Titanium tetrachloride (2.58 ml, 23.4 mmol) was added dropwise to a solution of pyridine (7.60 ml, 93.6 mmol) in 1,2-dichloroethane (40 ml) and, after completion of the addition, the reaction mixture was heated under reflux for 30 minutes in an argon atmosphere. After cooling of the reaction mixture, a solution of 3,5,6-trimethyl-2-(2-methyl-2-propenyl)-1,4-benzoquinone (2.40 g, 11.7 mmol) and aniline (3.35 ml, 35.1 mmol) in 1,2-dichloroethane (5 ml) was added thereto and the mixture was stirred at 90° C. for 2 hours in an argon atmosphere. The reaction mixture was cooled and filtered through Cerite and the filtrate was concentrated under reduced pressure. The residue was purified by silica gel column chromatography (hexane-ethyl acetate, 98:2). The resulting compound was dissolved in tetrahydrofuran (10 ml) and to the solution was added a solution of sodium hydrosulfite (12 g, 69 mmol) in water (30 ml). The mixture was stirred at room temperature for 30 minutes. The organic phase was separated and the aqueous phase was extracted with ethyl acetate. The extract was combined with the organic phase and the mixture was washed with water and dried and the solvent was distilled off under reduced pressure. The residue was purified by silica gel chromatography (hexane-ethyl acetate, 95:5) to obtain the desired compound as oil (1.41 g ield: 42.8%).

NMR (CDCl$_3$) δ1.80 (3E, s), 2.14 (6H, s), 2.19 (3H, s), 3.41 (2H, s), 4.69 (1H, s), 4.87 (1H, s), 5.03 (1H, s), 5.11

(1H, broad s), 6.42 (2H, d, J=7.4 Hz), 6.68 (1H, t, J=7.4 Hz), 7.13 (2H, t, J=7.4 Hz).

Experiment 1

Effect of drugs on the change of the behavior induced by spinal intrathecal injection of $FeCl_2$ in mice Male Slc: ICR mice (5 weeks) (10 mice per group) used. Saline (5 μl/mouse) containing 50 mM $FeCl_2$ was injected into the subarachnoid space between the 6th lumbar segment and the 1st sacral and scored as follows.

| Score | Behavioral |
|---|---|
| 0 : | normal |
| 1 : | vigorously biting lower extremity or lower abdomen |
| 2 : | a) extremely biting lower body with rolling |
|  | b) hyperreactive and aggressive to external stimuli |
|  | c) tremor |
|  | at least one of above three behavioral changes are observed |
| 3 : | clonic convulsion |
| 4 : | tonic convulsion or paralysis of one of both extremities |
| 5 : | death |

Percent inhibitions were calculated based on the scores evaluated above. The test compounds were orally administered 30 minutes prior to ferrous chloride injection.

Table 1 shows the mean scores and their percent inhibitions obtained by oral administration of 100 mg/kg of compound (I).

TABLE 1

| Test Compound Ex. No. | Mean Score | | % inhibition |
| | Administration of | | |
| | Test Compound of 100 mg/kg | Saline | |
|---|---|---|---|
| 103 | 0.1 | 4.9 | 98.0 |
| 1 | 1.2 | 4.6 | 73.9 |
| 84 | 0.5 | 4.6 | 89.1 |
| 47 | 1.0 | 4.9 | 79.6 |
| 85 | 0.6 | 4.6 | 87.0 |

The above results clearly show that the compounds of the present invention have superior depressant activity of central nervous system disorders caused by formation of lipoperoxide due to ferrous chloride.

As described hereinabove, the compounds (I) of the present invention have lipoperoxide formation inhibitory antioxidation) activity, and lipoxygenase and HHT formation inhibitory or suppression activity, and are useful as medicines for preventing and treating circulatory, inflammatory and allergic diseases.

What is claimed is:

1. A compound which is 4-formylamino-2,3,5-trimethyl-1-(2-methyl-2-propenyloxy)benzene.

2. A compound which is 4-formylamino-2,3,5-trimethyl-6-(2-methyl-2-propenyl)phenol.

\* \* \* \* \*